(12) United States Patent
Chang et al.

(10) Patent No.: US 8,481,537 B2
(45) Date of Patent: Jul. 9, 2013

(54) CASPASE INHIBITORS BASED OF PYRIDAZINONE SCAFFOLD

(75) Inventors: Hye Kyung Chang, Daejeon (KR); Yeong Soo Oh, Daejeon (KR); Yong Jin Jang, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 774 days.

(21) Appl. No.: 12/375,890

(22) PCT Filed: Jul. 27, 2007

(86) PCT No.: PCT/KR2007/003617
§ 371 (c)(1),
(2), (4) Date: Feb. 13, 2009

(87) PCT Pub. No.: WO2008/016239
PCT Pub. Date: Feb. 7, 2008

(65) Prior Publication Data
US 2009/0291959 A1 Nov. 26, 2009

(30) Foreign Application Priority Data

Aug. 2, 2006 (KR) .................. 10-2006-0073029

(51) Int. Cl.
*C07D 403/12* (2006.01)
*A61K 31/501* (2006.01)
*A61K 31/50* (2006.01)
*A61P 29/00* (2006.01)
*A61P 25/28* (2006.01)
*A61P 19/02* (2006.01)
*A61P 9/10* (2006.01)
*A61P 1/16* (2006.01)

(52) U.S. Cl.
USPC .............. 514/247; 514/252.05; 514/252.06; 544/238; 544/239; 544/240; 544/241

(58) Field of Classification Search
USPC .......... 544/232, 240, 239, 238, 241; 514/247, 514/252.05, 252.06
See application file for complete search history.

(56) References Cited

U.S. PATENT DOCUMENTS
6,225,288 B1    5/2001    Han et al.

FOREIGN PATENT DOCUMENTS
WO    WO-2004/069773 A1    8/2004
WO    WO 2004/106304 A2    12/2004

OTHER PUBLICATIONS

Zhang, et al., J. Neurosci., 2001, vol. 21, 1-6.*
Ray, Current Med. Chem., 13: 28, Dec. 2006; 3425-3440(16).*
Vincent, et al., Diabetes, Jan. 2007, vol. 56, # 1, 224-230.*
Fiorucci, et a., Aliment Pharmacol. Ther. 1999, 13, 421-435.*
Ranolleau, et al., J. Neurochem., vol. 100, # 4, 1062-1071, Feb. 2007.*
Pockros, et al., Nature Clinical Practice Gastroenterology & Hepatology (2007) 4, 588.*
Thornberry et al., "Inactivation of Interleukin-l.beta. Converting Enzyme by Peptide (Acyloxy)methyl Ketones", Biochemistry, 1994, vol. 33 No. 13, pp. 3934-3940.
Han et al., "Novel Pyrazinone Mono-amides as Potent and Reversible Caspase-3 Inhibitors," Bioorganic & Medicinal Chemistry Letters, vol. 15, 2005, pp. 1173-1180, XP025314426 (Available online Jan. 7, 2005).
Semple et al., "Pyridone-based Peptidomimetic Inhibitors of Interleukin-1β-Converting Enzyme (ICE)," Bioorganic & Medicinal Chemistry Letters, vol. 7, No. 10, 1997, pp. 1337-1342, XP004136329.

* cited by examiner

Primary Examiner — Susanna Moore
Assistant Examiner — Cecilia M Jaisle
(74) Attorney, Agent, or Firm — Birch, Stewart, Kolasch & Birch, LLP

(57) ABSTRACT

The present invention relates to a pyridazinone derivative which can be used as a caspase inhibitor, process for the preparation thereof, and pharmaceutical composition for inhibiting caspase comprising the same.

9 Claims, No Drawings

CASPASE INHIBITORS BASED OF PYRIDAZINONE SCAFFOLD

TECHNICAL FIELD

The present invention relates to a pyridazinone derivative or pharmaceutically acceptable salt thereof as an inhibitor against various caspases including caspase-1 [interleukin-1β-converting enzyme, ICE], caspase-3 [apopain/CPP-32], caspase-8, and caspase-9, and a pharmaceutical composition for the inhibition of caspase comprising the same.

BACKGROUND ART

Caspase is a new kind of cysteine protease in the form of $\alpha_2\beta_2$ tetramer discovered during the last 10 years. About 14 kinds thereof have been known until now. Caspase-1(ICE), one of them, is a kind of cytokine and participates in converting the biologically inactive prointerleukin-1β to the active interleukin-1β. Interleukin-1 consists of interleukin-1α and interleukin-1β, both of which are synthesized in monocytes in the form of 31 KDa precursor. Only prointerleukin-1β is activated by ICE. The positions hydrolyzed by caspase-1 are $Asp^{27}$-$Gly^{28}$ and $Asp^{116}$-$Ala^{117}$. The hydrolysis of the latter position gives interleukin-1β. Interleukin-1β has been reported to act as an important mediator in causing inflammation (1,3). Caspase-1 has been discovered for the first time in 1989, and the three dimensional structure thereof was determined by X-ray crystallographic method by two independent study groups.

Caspase-3(CPP-32) is broadly studied for its role or mechanism for action, and its three dimensional structure was determined in 1996(2). Caspase-3(apopain) activated from procaspase-3 is hydrolyzed in the position of $(P_4)$Asp-X-X-Asp$(P_1)$ motif, and the known substrates include poly(ADP-ribose) polymerase, U1 70,000 Mr small nuclear ribonucleoprotein, catalytic subunit of 460,000 Mr DNA-dependent protein kinase, etc. The X-ray structure of caspase-7 has been reported to be very similar to that of caspase-3(4).

Caspase-8 and 9 are present in the upstream of caspase-3, 6,7, and all of these caspases are known to participate in the apoptosis cascade. The X-ray structure of caspase-8 was determined in 1999(5), and particularly the inhibitors thereof may be advantageously used for treating the diseases related to apoptosis.

Caspase inhibitors mean those compounds that inhibit the activity of caspase, and so control such symptoms as inflammation, apoptosis, etc. caused by the caspase activity. Diseases or symptoms that may be treated or attenuated by administering the inhibitors include the following: dementia, cerebral stroke, brain impairment due to AIDS, diabetes, gastric ulcer, cerebral injury by hepatitis virus, hepatitis-induced hepatic diseases, acute hepatitis, fulminant hepatic failure, sepsis, organ transplantation rejection, rheumatic arthritis, ischemic cardiac diseases, and liver cirrhosis(6).

Among the caspase inhibitors known until now, the most noted irreversible inhibitors are the following:

IDN-1965

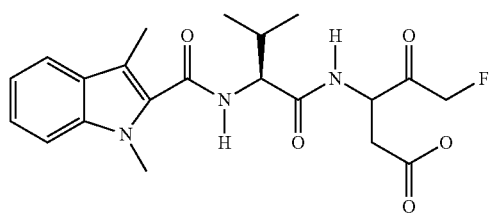

MX-1013

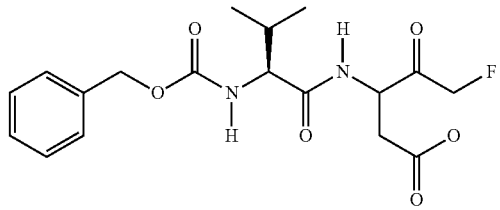

Both the above inhibitors exhibit their activity based on the common mechanism that they irreversibly inactivate the enzyme to suppress the cell apoptosis (irreversible, broad-spectrum inhibitor). It has been reported that irreversible inhibitor has much more effective inhibitory activity than reversible inhibitor (7). Both IDN-1965 of IDUN Co. and MX-1013 of Maxim Co. are reported to show activity in cell apoptosis model for hepatic injury (8, 9). These compounds are now in the stage of preclinical test. The irreversible inhibitor IDN-6556 is now in the stage of phase II clinical trial as a therapeutic agent for hepatic injury (10, 11).

IDN-6556

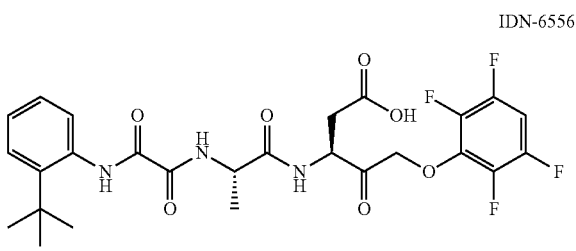 [SMILES: C[C@H](NC(=O)C(=O)Nc1ccccc1C(C)(C)C)C(=O)N[C@@H](CC(=O)O)C(=O)COc1c(F)c(F)cc(F)c1F]

REFERENCES (1) *Inflammation: Basic Principles and Clinical Correlates*, 2nd ed., ed by Gallin, Goldstein and Snyderman. Raven Press Ltd., New York. 1992, pp 211-232; *Blood*, 1996, 87(6), 2095-2147.

(2) Wilson, K. P. et al, *Nature*, 1994, 370. 270; Walker, N. P. C. et al. *Cell*, 1994, 78, 343; *Nature Structural Biology*, 1996, 3(7), 619.

(3) Thornberry, N. A. et al, *Nature*, 1992, 356. 768; *Nature Biotechnology*, 1996, 14, 297; *Protein Science*, 1995, 4, 3; *Nature*, 1995, 376(July 6), 37; *Protein Science*, 1995, 4, 2149.

(4) Wei, Y. et al, *Chemistry and Biology*, 2000, 7, 423.

(5) Blanchard H. et al, *Structure*, 1999, 7, 1125; Blanchard H. et al, *J. of Mol. Biol.*, 2000, 302, 9.

(6) References for caspase related diseases

Dementia: Arch Neurol 2003 March; 60(3):369-76, Caspase gene expression in the brain as a function of the clinical progression of Alzheimer disease. Pompl P N, Yemul S, Xiang Z, Ho L, Haroutunian V, Purohit D, Mohs R, Pasinetti G M.

Cerebral stroke: Proc Natl Acad Sci USA 2002 Nov. 12; 99(23):15188-93, Caspase activation and neuroprotection in caspase-3-deficient mice after in vivo cerebral ischemia and in vitro oxygen glucose deprivation. Le D A, Wu Y, Huang Z, Matsushita K, Plesnila N, Augustinack J C, Hyman B T, Yuan J, Kuida K, Flavell R A, Moskowitz M A.

Brain impairment due to AIDS: J Neurosci 2002 May 15; 22(10):4015-24, Caspase cascades in human immunodeficiency virus-associated neurodegeneration. Garden G A, Budd S L, Tsai E, Hanson L, Kaul M, D'Emilia D M, Friedlander R M, Yuan J, Masliah E, Lipton S A.

Diabetes: Diabetes 2002 June; 51(6):1938-48, Hyperglycemia-induced apoptosis in mouse myocardium: mitochondrial cytochrome C-mediated caspase-3 activation pathway. Cai L, Li W, Wang G, Guo L, Jiang Y, Kang Y J.

Gastric ulcer: J Physiol Pharmacol 1998 December; 49(4): 489-500, Role of basic fibroblast growth factor in the suppression of apoptotic caspase-3 during chronic gastric ulcer healing. Slomiany B L, Piotrowski J, Slomiany A.

Cerebral injury by hepatitis virus: J Viral Hepat 2003 March; 10(2):81-6, Cerebral dysfunction in chronic hepatitis C infection. Forton D M, Taylor-Robinson S D, Thomas H C.

Fulminant hepatic failure: Gastroenterology 2000 August; 119(2):446-60, Tumor necrosis factor alpha in the pathogenesis of human and murine fulminant hepatic failure. Streetz K, Leifeld L, Grundmann D, Ramakers J, Eckert K, Spengler U, Brenner D, Manns M, Trautwein C.

Sepsis: Nat Immunol 2000 December; 1(6):496-501, Caspase inhibitors improve survival in sepsis: a critical role of the lymphocyte. Hotchkiss R S, Chang K C, Swanson P E, Tinsley K W, Hui J J, Klender P, Xanthoudakis S, Roy S, Black C, Grimm E, Aspiotis R, Han Y, Nicholson D W, Karl I E.

Organ transplantation rejection: Xenotransplantation 2001 May; 8 (2):115-24, In vitro prevention of cell-mediated xeno-graft rejection via the Fas/FasL-pathway in CrmA-transducted porcine kidney cells. Fujino M, Li X K, Suda T, Hashimoto M, Okabe K, Yaginuma H, Mikoshiba K, Guo L, Okuyama T, Enosawa S, Amemiya H, Amano T, Suzuki S.

Rheumatic arthritis: Prog Med Chem 2002; 39:1-72, Caspase inhibitors as anti-inflammatory and antiapoptotic agents. Graczyk P P.

Ischemic cardiac diseases: Am J Physiol Heart Circ Physiol 2002 September; 283(3):H990-5, Hypoxia-induced cleavage of caspase-3 and DFF45/ICAD in human failed cardiomyocytes. Todor A, Sharov V G, Tanhehco E J, Silverman N, Bernabei A, Sabbah H N.

Anti-inflammation: J Immunol 2003 Mar. 15; 170(6):3386-91, A broad-spectrum caspase inhibitor attenuates allergic airway inflammation in murine asthma model. Iwata A, Nishio K, Winn R K, Chi E Y, Henderson W R Jr, Harlan J M.

Hepatitis-induced hepatic diseases: i) J Viral Hepat. 2003 September; 10(5):335-42. Apoptosis in hepatitis C Kountouras J, Zavos C, Chatzopoulos D.; ii) Apoptosis. 2003 December; 8 (6):655-63. Apoptosis participates to liver damage in HSV-induced fulminant hepatitis. Pretet J L, Pelletier L, Bernard B, Coumes-Marquet S, Kantelip B, Mougin C.; iii) Proc Natl Acad Sci USA. 2003 Jun. 24; 100(13):7797-802. Caspase 8 small interfering RNA prevents acute liver failure in mice. Zender L, Hutker S, Liedtke C, Tillmann H L, Zender S, Mundt B, Walternathe M, Gosling T, Flemming P, Malek N P, Trautwein C, Manns M P, Kuhnel F, Kubicka S.

Liver cirrhosis: i) J Pharmacol Exp Ther. 2004 March; 308 (3):1191-6, The caspase inhibitor Idn-6556 attenuates hepatic injury and fibrosis in the bile duct ligated mouse. Canbay A., Fledstein A., Baskin-Bey E., Bronk F S. Gores G J.; ii) Hepatology. 2004 February; 39(2):273-8, Apoptosis: the nexus of liver injury and fibrosis. Canbay A, Friedman S, Gores G J.; iii) Hepatology. 2003 November; 38 (5):1 188-98, Kupffer cell engulfment of apoptotic bodies stimulates death ligand and cytokine expression. Canbay A, Feldstein A E, Higuchi H, Werneburg N, Grambihler A, Bronk S F, Gores G J.

(7) Wu J. et al, *Methods: A Companion to Methods in Enzymology*, 1999, 17, 320.

(8) Hoglen N. C. et al, *J. of Pharmacoloy and Experimental Therapeutics*, 2001, 297, 811.

(9) Jaeschke H. et al, *Toxicology and Applied Pharmacology*, 2000, 169, 77.

(10) Hoglen N. C. et al, *J. Pharmacol Exp. Ther.*, 2004, 309(2):634. Characterization of IDN-6556 (3-[2-(2-tert-butyl-phenylaminooxalyl)-amino]-propionylamino]-4-oxo-5-(2,3,5,6-tetrafluoro-phenoxy)-pentanoic acid): a liver-targeted caspase inhibitor.

(11) Canbay A. et al, *J. Pharmacol. Exp. Ther,* 2004, 308 (3), 1191. The caspase inhibitor IDN-6556 attenuates hepatic injury and fibrosis in the bile duct ligated mouse.

DETAILED DESCRIPTION OF INVENTION

Technical Subject

The present inventors have extensively studied to design novel compounds which can be used as an effective and more selective inhibitor against caspases.

Means for Solving the Subject

To achieve such a subject, the present inventors synthesized various compounds, and determined their binding ability and inhibitory activity for caspases. As a result, the inventors have discovered that a compound of the following formula (1) does meet such requirements, and completed the present invention.

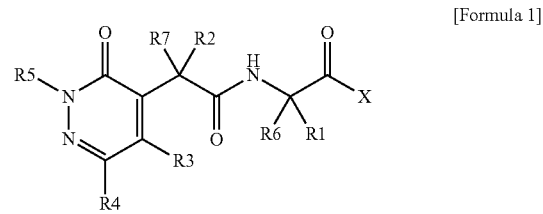

[Formula 1]

in which

R, $R^1$, $R^2$, $R^3$, $R^4$, $R^5$, $R^6$, $R^7$ and X are defined below.

Therefore, the present invention provides the novel pyridazinone derivative of formula (1) or pharmaceutically acceptable salt thereof having effective inhibitory activity against caspases.

It is another object of the present invention to provide a pharmaceutical composition for inhibiting caspase, specifically a composition for preventing inflammation and apoptosis, comprising the compound of formula (1) or pharmaceutically acceptable salt thereof as an active ingredient together with the pharmaceutically acceptable carrier.

Advantageous Effect

The compound of formula (I) according to the present invention has an excellent inhibitory activity against caspase, and so can be advantageously used for the treatment of various diseases and symptoms mediated by caspase.

Best Mode for Carrying Out the Invention

First of all, the important terms in the present invention are defined as follows:

a) $C_1$-$C_5$-alkyl: Straight-chain or branched hydrocarbons having 1 to 5 carbon atoms, that include methyl, ethyl, n-propyl, i-propyl, n-butyl, i-butyl, t-butyl, etc., but are not limited thereto.

b) $C_3$-$C_{10}$-cycloalkyl: Cyclic hydrocarbons having 3 to 10 carbon atoms, that include cyclopropyl, cyclobutyl, cyclopentyl, cyclohexyl, etc., but are not limited thereto.

c) Aryl: Aryl group includes all the aromatic, heteroaromatic and their partially reduced derivatives. The aromatic group means a 5 to 15-membered single or fused unsaturated hydrocarbon. The heteroaromatic group means the aromatic group containing 1 to 5 hetero atoms selected from a group consisting of oxygen, sulfur, and nitrogen. The aryl group includes phenyl, naphthyl, indolyl, quinolinyl, isoquinolyl, imidazolinyl, isoxazolyl, oxazolyl, thiazolyl, etc., but is not limited thereto.

One or more hydrogens in said $C_1$-$C_5$-alkyl, $C_3$-$C_{10}$-cycloalkyl or aryl group may be replaced with a group(s) selected from the following: acyl, amino, carboalkoxy, carboxy, carboxyamino, cyano, halo, hydroxy, nitro, thio, alkyl, cycloalkyl, alkoxy, aryl, aryloxy, sulfoxy, and guanido group.

d) Natural amino acid includes the following: Glycine, Alanine, Valine, Leucine, Isoleucine, Serine, Threonine, Cysteine, Methionine, Proline, Aspartic acid, Asparagine, Glutamic acid, Glutamine, Lysine, Arginine, Histidine, Phenylalanine, Tyrosine, and Tryptophan.

Further, the present specification includes the following abbreviations:

N-bromosuccinimide: NBS
O-(7-azabenzotriazol-1-yl)-N,N,N',N'-tetramethyluroniumhexafluorophosphate]: HATU
N,N-dimethyl formamide: DMF
Dimethylsulfoxide: DMSO
N-methylmorpholine: NMM
2,2'-Azobis(2-methyl propionitrile): AIBN
2,2,6,6-Tetramethyl-1-piperidinyloxy, free radical: TEMPO
Lithium bis(trimethylsilyl)amide: LiHMDS
N-(2-Hydroxyethyl)piperazine-N'-(2'-ethanesulfonic acid): HEPES
3-[(3-Cholamidopropyl)dimethylamino]-1-propanesulfonate: CHAPS
Ethylenediaminetetraacetic acid: EDTA
Dithiothreitol: DTT The present invention will be explained more in detail below. One aspect of the present invention relates to the pyridazinone derivative of the following formula (1):

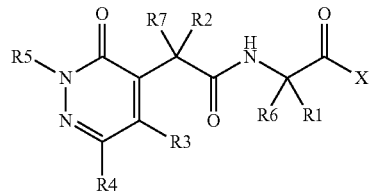

[Formula 1]

in which
I) $R^1$ represents H, $C_1$-$C_5$-alkyl, $C_3$-$C_{10}$-cycloalkyl, aryl, or a side chain residue of all the natural amino acids,
II) $R^2$ represents H, $C_1$-$C_5$-alkyl, $C_3$-$C_{10}$-cycloalkyl, aryl, or a side chain residue of all the natural amino acids,
III) $R^3$ represents H, $C_1$-$C_5$-alkyl, hydroxy, $C_1$-$C_5$-alkoxy, or halogen,
IV) $R^4$ represents H, $C_1$-$C_5$-alkyl, $C_3$-$C_{10}$-cycloalkyl, or aryl,
V) $R^5$ represents H, $C_1$-$C_5$-alkyl, $C_3$-$C_{10}$-cycloalkyl, or aryl,
☐) $R^6$ and $R^7$ independently of one another each represent H, $C_1$-$C_5$-alkyl, $C_3$-$C_{10}$-cycloalkyl, or aryl,
☐) X represents —$CH_2OR^9$ ($R^9$ is $C_1$-$C_5$-alkyl, $C_3$-$C_{10}$-cycloalkyl, or aryl), —$CH_2OC(=O)R^{10}$ ($R^{10}$ is $C_1$-$C_5$-alkyl, $C_3$-$C_{10}$-cycloalkyl, or aryl), —$CH_2$—$OP(=O)R_2^{11}$ ($R^{11}$ is $C_1$-$C_5$-alkyl, $C_3$-$C_{10}$-cycloalkyl, or aryl), or —$CH_2$—W (W is halogen), or pharmaceutically acceptable salt thereof, which is useful as an inhibitor for caspase.

In the compound of formula (1) according to the present invention, $R^1$ preferably represents a side chain residue of all the natural amino acids, more preferably —$CH_2COOH$. The compound of formula (1) may include the two kinds of stereoisomers, or mixtures thereof (diastereomeric mixtures) when the carbon to which $R^1$ is attached becomes a stereocenter due to the $R^1$ group. The compound of formula (I) may include an ester form (—$CO_2Y$ wherein Y is $C_1$-$C_5$-alkyl), a sulfonamide form (—$CONHSO_2Z$ wherein Z is $C_1$-$C_5$-alkyl), and a pharmaceutically acceptable salt form, when $R^1$ is a side chain residue of an amino acid containing carboxyl moiety; or the compound of formula (I) may also exist in the form of a pharmaceutically acceptable salt when $R^1$ is a side chain residue of an amino acid containing a base moiety.

The compound of the present invention (formula 1a) may exist in the form of a cyclic ketal (formula 1b) when $R^1$ is —$CH_2COOH$, and so a skilled artisan may understand that the cyclic ketal form (formula 1b) may also be covered by the present invention.

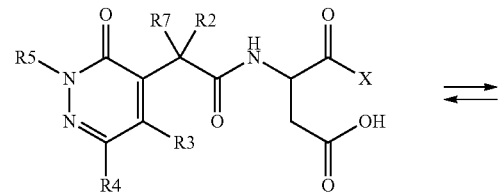

Formula 1a

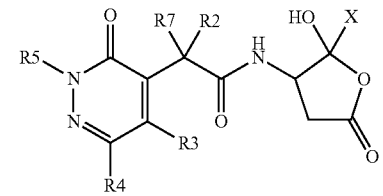

Formula 1b

Also, the equilibrium forms of said compounds should be understood to cover their tautomeric forms.

$R^2$ preferably represents $C_1$-$C_5$-alkyl, more preferably methyl, ethyl, n-propyl, i-propyl, n-butyl, i-butyl, or t-butyl. The compound of formula (I) may include the two kinds of stereoisomers, or mixtures thereof (diastereomeric mixtures) when the carbon to which $R^2$ is attached becomes a stereocenter due to the $R^2$ group. The compound of formula (I) may include an ester form (—$CO_2Y$ wherein Y is $C_1$-$C_5$-alkyl), a sulfonamide form (—$CONHSO_2Z$ wherein Z is $C_1$-$C_5$-alkyl), and a pharmaceutically acceptable salt form, when $R^2$ is a side chain residue of an amino acid containing carboxyl moiety; or the compound of formula (I) may also exist in the form of a pharmaceutically acceptable salt when $R^2$ is a side chain residue of an amino acid containing a base moiety.

$R^3$ preferably represents H, $C_1$-$C_5$-alkyl, $C_1$-$C_5$-alkoxy, or halogen, more preferably H, methyl, ethyl, n-propyl, i-propyl, n-butyl, i-butyl, or t-butyl, methoxy, ethoxy, fluoro, or chloro.

$R^4$ preferably represents H.

$R^5$ preferably represents $C_1$-$C_5$-alkyl substituted by substituted or unsubstituted $C_3$-$C_{10}$-cycloalkyl or by substituted or unsubstituted aryl; or represents substituted or unsubstituted aryl. $R^5$ more preferably represents $C_1$-$C_5$-alkyl substituted by $C_3$-$C_{10}$-cycloalkyl which is unsubstituted or substituted by one or more substituents selected from the group consisting of $C_1$-$C_5$-alkyl, hydroxy, $C_1$-$C_5$-alkoxy and halogen, or by aryl which is unsubstituted or substituted by one or more substituents selected from the group consisting of $C_1$-$C_5$-alkyl, hydroxy, $C_1$-$C_5$-alkoxy and halogen; or represents aryl which is unsubstituted or substituted by one or more substituents selected from the group consisting of $C_1$-$C_5$-alkyl, hydroxy, $C_1$-$C_5$-alkoxy and halogen. For example, $R^5$ is phenyl, naphthyl, indolyl, quinolinyl, isoquinolyl, imidazolinyl, isoxazolyl, oxazolyl or thiazolyl, or is methyl substituted by phenyl, naphthyl, indolyl, quinolinyl, isoquinolyl, imidazolinyl, isoxazolyl, oxazolyl, thiazolyl or cyclohexyl, each of which is unsubstituted or substituted by one or more substituents selected from the group consisting of methyl, ethyl, n-propyl, i-propyl, n-butyl, i-butyl, t-butyl, methoxy, ethoxy, trihalomethyl and halogen.

$R^6$ and $R^7$ each preferably represent H.

$R^9$ preferably represents aryl substituted by one or more halogens, more preferably phenyl substituted by one or more fluorines, and most preferably 2,3,5,6-tetrafluorophenyl, 2,3,6-trifluorophenyl or 2,6-difluorophenyl.

$R^{10}$ preferably represents aryl substituted by one or more halogens, more preferably phenyl substituted by one or more chlorines, most preferably 2,6-dichlorophenyl.

$R^{11}$ preferably represents aryl, more preferably phenyl.

W preferably represents F.

The most preferred compounds are those selected from the following group:

5-fluoro-3-[2-(5-methyl-3-oxo-2-phenyl-2,3-dihydro-pyridazin-4-yl)-butyrylamin o]-4-oxo-pentanoic acid (1);

3-[2-(2-benzyl-5-methyl-3-oxo-2,3-dihydro-pyridazin-4-yl)-butyrylamino]-5-fluor o-4-oxo-pentanoic acid (2);

3-[2-(2-benzyl-3-oxo-2,3-dihydro-pyridazin-4-yl)-butyrylamino]-5-fluoro-4-oxo-pentanoic acid (3);

3-[2-(2-benzyl-5-chloro-3-oxo-2,3-dihydro-pyridazin-4-yl)-butyrylamino]-5-fluor o-4-oxo-pentanoic acid (4);

3-[2-(2-benzyl-5-methoxy-3-oxo-2,3-dihydro-pyridazin-4-yl)-butyrylamino]-5-flu oro-4-oxo-pentanoic acid (5);

3-2-[2-(2-tert-butyl-benzyl)-3-oxo-2,3-dihydro-pyridazin-4-yl]-butyrylamino-5-fl uoro-4-oxo-pentanoic acid (6);

3-2-[2-(3-tert-butyl-benzyl)-3-oxo-2,3-dihydro-pyridazin-4-yl]-butyrylamino-5-fl uoro-4-oxo-pentanoic acid (7);

5-fluoro-3-2-[2-(2-methyl-benzyl)-3-oxo-2,3-dihydro-pyridazin-4-yl]-butyrylamin o-4-oxo-pentanoic acid (8);

5-fluoro-3-2-[2-(3-methyl-benzyl)-3-oxo-2,3-dihydro-pyridazin-4-yl]-butyrylamin o-4-oxo-pentanoic acid (9);

5-fluoro-3-2-[2-(3-methoxy-benzyl)-3-oxo-2,3-dihydro-pyridazin-4-yl]-butyrylam ino-4-oxo-pentanoic acid (10);

5-fluoro-3-[2-(2-naphthalen-1-ylmethyl-3-oxo-2,3-dihydro-pyridazin-4-yl)-butyry l amino]-4-oxo-pentanoic acid (11);

5-fluoro-3-[2-(2-naphthalen-2-ylmethyl-3-oxo-2,3-dihydro-pyridazin-4-yl)-butyry l amino]-4-oxo-pentanoic acid (12);

5-fluoro-3-2-[2-(2-methyl-oxazol-4-ylmethyl)-3-oxo-2,3-dihydro-pyridazin-4-yl]-butyrylamino-4-oxo-pentanoic acid (13);

5-fluoro-3-2-[2-(2-methyl-thiazol-4-ylmethyl)-3-oxo-2,3-dihydro-pyridazin-4-yl]-butyrylamino-4-oxo-pentanoic acid (14);

3-2-[2-(3,5-dimethyl-isoxazol-4-ylmethyl)-3-oxo-2,3-dihydro-pyridazin-4-yl]-but yryl amino-5-fluoro-4-oxo-pentanoic acid (15);

3-[2-(2-cyclohexylmethyl-3-oxo-2,3-dihydro-pyridazin-4-yl)-butyrylamino]-5-flu oro-4-oxo-pentanoic acid (16);

5-fluoro-3-[2-(2-isoquinolin-1-ylmethyl-3-oxo-2,3-dihydro-pyridazin-4-yl)-butyry l amino]-4-oxo-pentanoic acid (17);

3-{2-[2-(2-chloro-benzyl)-3-oxo-2,3-dihydro-pyridazin-4-yl]-butyrylamino}-5-flu oro-4-oxo-pentanoic acid (18);

3-{2-[2-(3-chloro-benzyl)-3-oxo-2,3-dihydro-pyridazin-4-yl]-butyrylamino}-5-flu oro-4-oxo-pentanoic acid (19);

3-{2-[2-(3-bromo-benzyl)-3-oxo-2,3-dihydro-pyridazin-4-yl]-butyrylamino}-5-flu oro-4-oxo-pentanoic acid (20);

5-fluoro-4-oxo-3-{2-[3-oxo-2-(2-trifluoromethyl-benzyl)-2,3-dihydro-pyridazin-4-yl]-butyrylamino}-pentanoic acid (21);

5-fluoro-4-oxo-3-{2-[3-oxo-2-(3-trifluoromethyl-benzyl)-2,3-dihydro-pyridazin-4-yl]-butyrylamino}-pentanoic acid (22);

2,6-dichloro-benzoic acid (S)-3-{(R)-2-[2-(2-tert-butyl-benzyl)-3-oxo-2,3-dihydro-pyridazin-4-yl]-butyrylamino}-4-carboxy-2-oxo-butyl ester and 2,6-dichloro-benzoic acid (S)-3-{(S)-2-[2-(2-tert-butyl-benzyl)-3-oxo-2,3-dihydro-pyridazin-4-yl]-butyrylamino}-4-carboxy-2-oxo-butyl ester (23-1, 23-2);

(S)-3-{(R)-2-[2-(2-tert-butyl-benzyl)-3-oxo-2,3-dihydro-pyridazin-4-yl]-butyryla mino}-4-oxo-5-(2,3,5,6-tetrafluoro-phenoxy)-pentanoic acid and (S)-3-{(S)-2-[2-(2-tert-butyl-benzyl)-3-oxo-2,3-dihydro-pyridazin-4-yl]-butyrylamino}-4-oxo-5-(2,3,5,6-tetrafluoro-phenoxy)-pentanoic acid (24-1, 24-2);

(S)-3-{(R)-2-[2-(3-tert-butyl-benzyl)-3-oxo-2,3-dihydro-pyridazin-4-yl]-butyryla mino}-4-oxo-5-(2,3,5,6-tetrafluoro-phenoxy)-pentanoic acid and (S)-3-{(S)-2-[2-(3-tert-butyl-benzyl)-3-oxo-2,3-dihydro-pyridazin-4-yl]-butyrylamino}-4-oxo-5-(2,3,5,6-tetrafluoro-phenoxy)-pentanoic acid (25-1, 25-2);

(S)-3-{(R)-2-[2-(2-tert-butyl-benzyl)-3-oxo-2,3-dihydro-pyridazin-4-yl]-butyryla mino}-4-oxo-5-(2,3,6-trifluoro-phenoxy)-pentanoic acid and
(S)-3-{(S)-2-[2-(2-tert-butyl-benzyl)-3-oxo-2,3-dihydro-pyridazin-4-yl]-butyrylamino}-4-oxo-5-(2,3,6-trifluoro-phenoxy)-pent anoic acid (26-1, 26-2);
(S)-3-{(R)-2-[2-(2-tert-butyl-benzyl)-3-oxo-2,3-dihydro-pyridazin-4-yl]-butyryla mino}-5-(2,6-difluoro-phenoxy)-4-oxo-pentanoic acid and
(S)-3-{(S)-2-[2-(2-tert-butyl-benzyl)-3-oxo-2,3-dihydro-pyridazin-4-yl]-butyrylamino}-5-(2,6-difluoro-phenoxy)-4-oxo-pentanoic acid (27-1, 27-2); and
(S)-3-{2-[2-(2-tert-butyl-benzyl)-3-oxo-2,3-dihydro-pyridazin-4-yl]-butyrylamino}-5-(diphenyl-phosphinoy-loxy)-4-oxo-pentanoic acid (28).

The processes for preparation of the novel pyridazinone derivative of formula (1) showing an inhibitory activity against caspases are depicted in the following Reaction Schemes 1 to 4. However, those illustrated in the following Reaction Schemes represent only the typical processes used in the present invention. The manipulation order, reagent, reaction condition, solvent, etc. may be changed with no limit.

compound (4). Then, the aldehyde compound (4) and hydrazine hydrate are reacted in a suitable solvent, for example ethanol, to give a dihydropyridazinone compound (5). The dihydropyridazinone compound (5) is oxidized with a suitable oxidizing agent, for example thionyl chloride, in a suitable solvent, for example methylene chloride, to give the desired compound of pyridazinone structure (6).

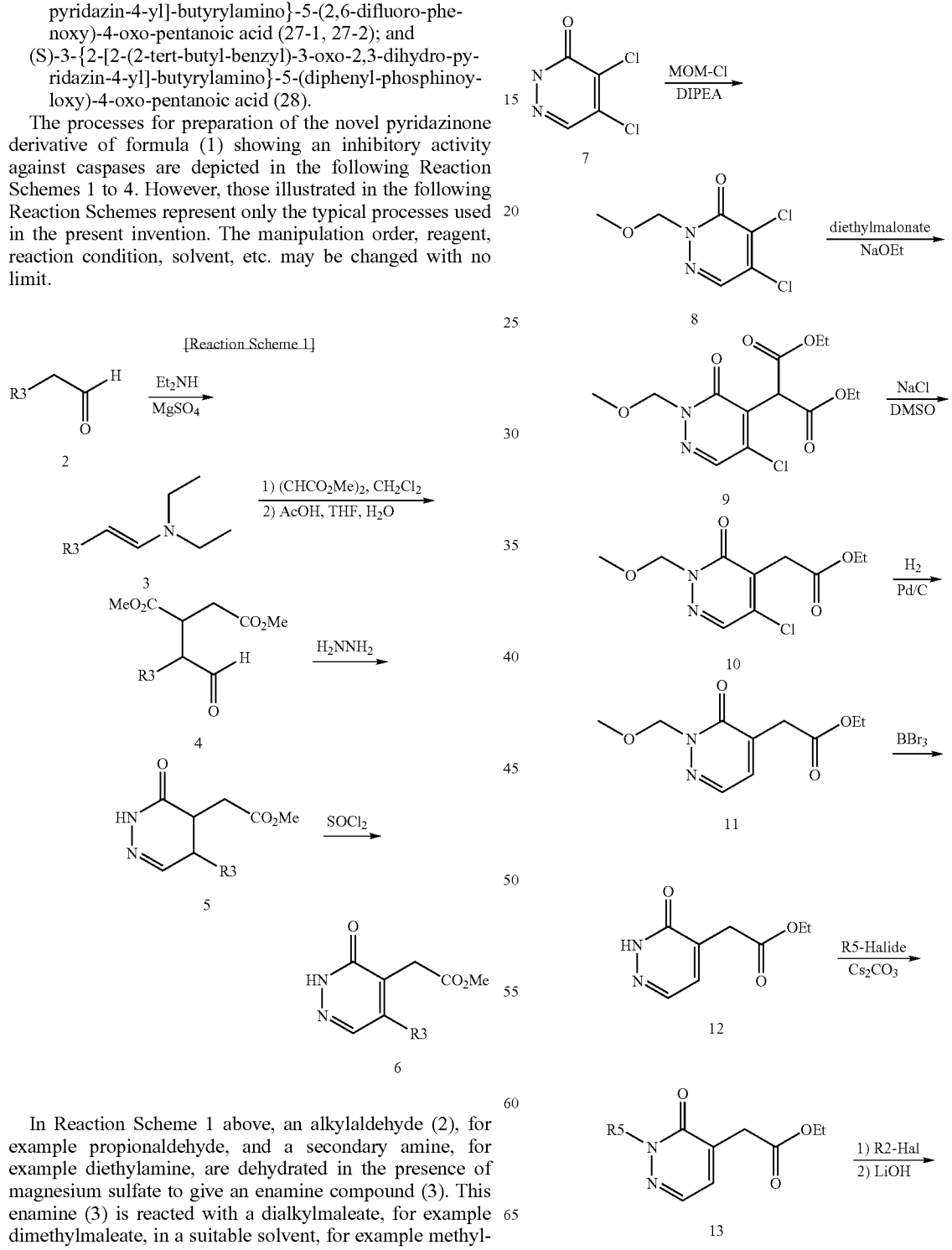

In Reaction Scheme 1 above, an alkylaldehyde (2), for example propionaldehyde, and a secondary amine, for example diethylamine, are dehydrated in the presence of magnesium sulfate to give an enamine compound (3). This enamine (3) is reacted with a dialkylmaleate, for example dimethylmaleate, in a suitable solvent, for example methylene chloride, and treated with acetic acid to give an aldehyde

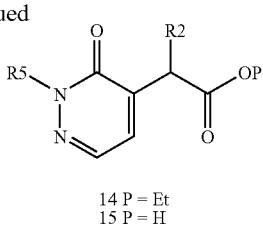

14 P = Et
15 P = H

In Reaction Scheme 2 above, 4,5-dichloro-3(2H)-pyridazinone (7) is protected by methoxymethyl protecting group (8), and reacted with diethylmalonate and sodium ethoxide to give a derivative of diethyl malonate (9). The derivative (9) is heated with NaCl in DMSO to give monoacetate (10). The monoacetate thus obtained (10) is treated with Pd/C under hydrogen atmosphere to synthesize the derivative (11). This derivative (11) is deprotected by using $BBr_3$, and the resulting derivative (12) is reacted with a suitable alkyl halide to give the derivative (13). This derivative (13) is reacted with LiHMDS and a suitable alkyl halide to give the derivative (14), which is further hydrolyzed, if necessary, to give the carboxylic acid derivative (15) having no protecting group.

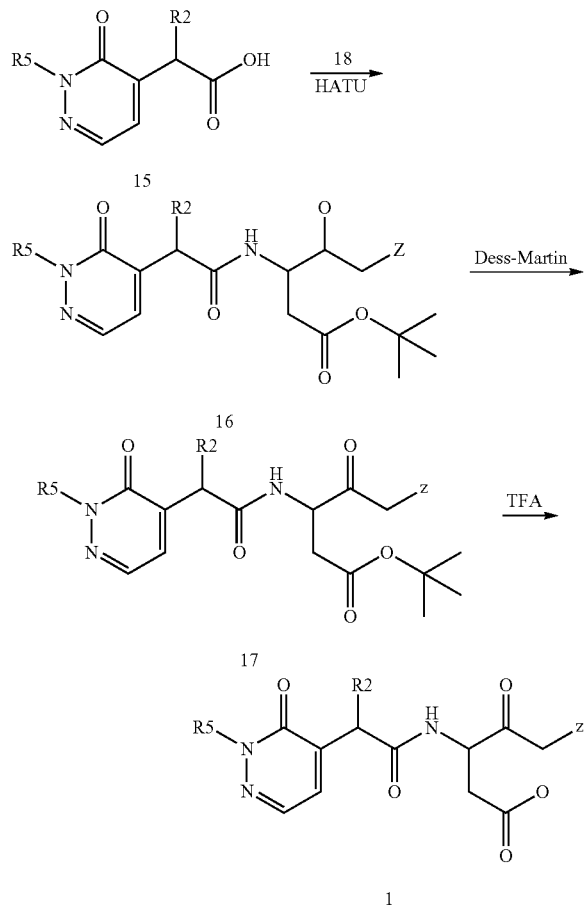

In Reaction Schemes 3 and 4, Z represents —$OR^9$ ($R^9$ is $C_1$-$C_5$-alkyl, $C_3$-$C_{10}$-cycloalkyl or aryl), —OC(=O)$R^{10}$ ($R^{10}$ is $C_1$-$C_5$-alkyl, $C_3$-$C_{10}$-cycloalkyl or aryl), or —W (W is halogen).

As depicted in Reaction Scheme 3 above, the carboxylic acid derivative (15) is coupled with the aspartic acid derivative (18) (see the following Reaction Scheme 4) to give the compound (16), which is then subjected to Dess-Martin periodene oxidation reaction, and deprotection reaction, if needed, to give the desired compound of formula (1).

The functional group Z in the compound (1) of Reaction Scheme 3 may be formed first by synthesizing the compound (18) already having the desired Z group according to the process of Reaction Scheme 4, and by reacting the compound (18) with the carboxylic acid compound (15) (see WO 00/23421). Or, the desired Z group may be introduced later according to the process of Reaction Scheme 4 after the carboxylic acid compound (15) is combined with the aspartic acid (β-t-Bu) methyl ester and hydrolyzed. When Z is F, the racemic compound may be prepared according to a method known in *Tetrahedron Letters*, 1994, 35(52), 9693-9696.

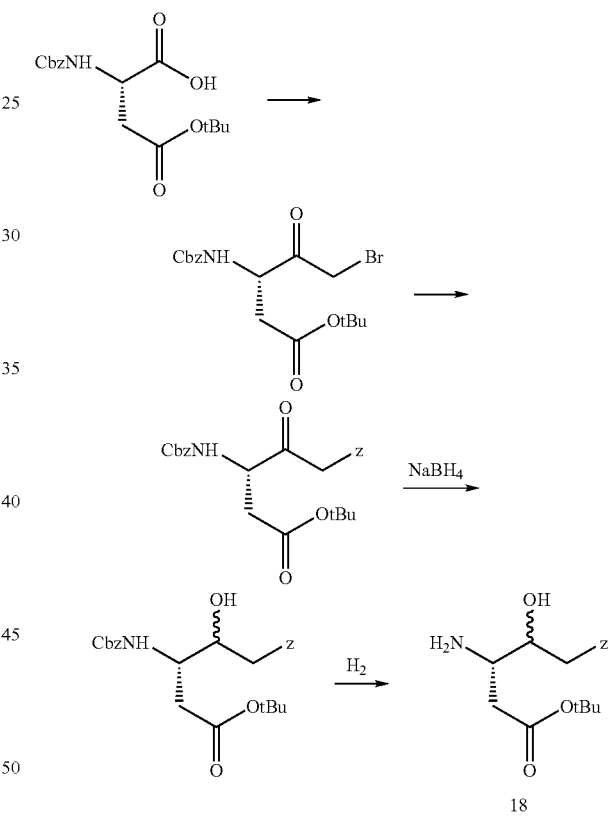

The compound of formula (1) according to the present invention has a broad spectrum of inhibitory activity against caspases as demonstrated by the results of the following Experiments, and so has an effect for preventing inflammation and apoptosis. Thus, the present invention provides a pharmaceutical composition for inhibiting caspases, specifically a therapeutic composition for preventing inflammation and apoptosis, comprising the compound of formula (1) or pharmaceutically acceptable salt thereof as an active ingredient together with the pharmaceutically acceptable carrier. Specifically, the composition of the present invention has a therapeutic or preventing effect for dementia, cerebral stroke, brain impairment due to AIDS, diabetes, gastric ulcer, cerebral injury by hepatitis, hepatitis-induced hepatic diseases, acute hepatitis, fulminant hepatic failure, sepsis, organ transplantation rejection, rheumatic arthritis, cardiac cell apoptosis due to ischemic cardiac diseases, or liver cirrhosis.

The compound of formula (1) may be formulated into various pharmaceutical forms for administration purpose. To prepare the pharmaceutical composition according to the present invention, an effective amount of the compound of formula (I) or pharmaceutically acceptable salt thereof is mixed with a pharmaceutically acceptable carrier that may take a wide variety of forms depending on the formulation to be prepared.

The caspase inhibitor compound may be formulated as a parenteral injection, or percutaneous or oral preparation, depending on its application purpose. It is especially advantageous to formulate the composition in a unit dosage form for ease of administration and uniformity of dosage.

For the oral preparation, any usual pharmaceutical carrier may be used. For example, water, glycols, oils, alcohols and the like may be used for such oral liquid preparations as suspensions, syrups, elixirs and solutions; or starches, sugars, kaolin, lubricants, binders, disintegrating agents and the like may be used for such solid preparations as powders, pills, capsules and tablets. Due to their ease of administration, tablets and capsules are the most advantageous dosage unit forms. It is also desirable for tablets and pills to be formulated into enteric-coated preparation.

For the parenteral preparation, sterile water is usually used as the carrier, though other ingredients such as solubility aids may be used. Injections, for example, sterilized aqueous or oily suspension for injection, can be prepared according to the known procedure using suitable dispersing agent, wetting agent, or suspending agent. Solvents that can be used for preparing injections include water, Ringer's fluid, and isotonic NaCl solution, and also sterilized fixing oil may be conveniently used as the solvent or suspending media. Any non-stimulative fixing oil including mono- or di-glyceride may be used for this purpose. Fatty acid such as oleic acid may also be used for injections.

For the percutaneous administration, the carrier may include a penetration enhancing agent and/or a suitable wetting agent, optionally combined with suitable additives having no significant skin irritation. Said additives may facilitate the administration through the skin and/or may assist preparation of a desired composition. These percutaneous preparations are administered via various manners, e.g., as a transdermal patch, a spot-on, or an ointment.

When the caspase inhibitor of the present invention is used for clinical purpose, it is preferable to administer to the subject patient in an amount ranging from 0.1 to 100 mg per kg of body weight a day. The total daily dosage may be administered once or over several times. However, specific administration dosage for an individual patient can be varied with specific compound used, body weight, gender, hygienic condition, or diet of subject patient, time or method of administration, excretion rate, mixing ratio of agent, severity of disease to be treated, etc.

Embodiments for Practicing the Invention

The present invention will be more specifically explained by the following examples. However, it should be understood that these examples are intended to illustrate the present invention but not in any manner to limit the scope of the present invention.

Preparation 1-1)

(5-Methyl-3-oxo-2,3,4,5-tetrahydro-pyridazin-4-yl)-acetic acid methyl ester

Magnesium sulfate (3.6 kg, 30.0 mol) was introduced into diethylamine (6.6 kg, 90.0 mol), to which was added propionaldehyde (1.76 kg, 30.3 mol) with maintaining a temperature of 0° C. The mixture was warmed to room temperature, and stirred for 2.5 h. To this mixture was introduced 18 L of methylene chloride, which was then cooled to 0° C. Dimethylmaleate (3.04 kg, 21.1 mol) was added, and the resulting mixture was stirred for 20 h. The reaction mixture was filtered to remove the solid, and the filtrate was distilled under reduced pressure to give crude 3-diethylamino-4-methyl-cyclobutane-1,2-dicarboxylic acid dimethyl ester.

To 3-diethylamino-4-methyl-cyclobutane-1,2-dicarboxylic acid dimethyl ester obtained above were added tetrahydrofuran (10 L) and distilled water (5 L), acetic acid (2.54 kg, 42.3 mol) was added thereto, and the mixture was stirred under reflux for 1 h. Tetrahydrofuran was removed by distillation under reduced pressure. Ethyl acetate was added to the residue, which was then extracted-dried-concentrated according to a conventional manner to give crude 2-(1-methyl-2-oxo-ethyl)succinic acid dimethyl ester (3.44 kg).

To this 2-(1-methyl-2-oxo-ethyl)succinic acid dimethyl ester was added ethanol (13 L), which was cooled to 0° C. Acetic acid (1.2 kg, 20 mol) was added with maintaining the temperature. To the reaction mixture was added hydrazine hydrate (1.08 kg, 21.6 mol), which was warmed to room temperature and stirred for 16 h. Ethanol was removed by distillation under reduced pressure, methylene chloride was added to the residue, which was then extracted-dried-concentrated according to a conventional manner to give the title compound (2.80 kg, Yield: 51%).

$^1$H-NMR (CDCl$_3$, 500 MHz) δ ☐8.39 (br s, 1H), 7.17 (d, 0.5H), 6.94 (s, 0.5H), 3.71 (d, 3H), 3.20-3.15 (m, 0.5H), 3.03-2.98 (m, 0.5H), 2.78-2.73 (m, 1H), 2.67-2.61 (m, 1H), 2.39-2.34 (m, 0.5H), 1.24 (d, 0.5H), 1.01 (d, 1.5H)

Preparation 1-2)

(5-Methyl-3-oxo-2,3-dihydro-pyridazin-4-yl)-acetic acid methyl ester

To the compound of Preparation 1-1) (2.70 kg, 14.7 mol) was added methylene chloride (27 L), which was then cooled to 0° C. Thionyl chloride (2.08 kg, 17.6 mol) was added thereto over 40 min. The mixture was warmed to room temperature, and stirred for 4.5 h. To the reaction mixture were added 20 kg of 10% aqueous sodium chloride solution and 16 kg of methylene chloride. The organic layer obtained by phase separation was dried-concentrated according to a conventional manner to give the title compound (1.72 kg, Yield: 64%) as a pale yellow solid.

$^1$H-NMR (CDCl$_3$, 500 MHz) δ 12.08 (br s, 1H), 7.66 (s, 1H), 3.70 (s, 3H), 3.68 (s, 2H), 2.19 (s, 3H)

Preparation 1-3)

(5-Methyl-3-oxo-2-phenyl-2,3-dihydro-pyridazin-4-yl)-acetic acid methyl ester

To a mixture of the compound of Preparation 1-2) (182 mg, 1.0 mmol), phenylboronic acid (244 mg, 2.0 eq), Cu(OAc)$_2$.H$_2$O (40 mg, 0.2 eq), pyridine (0.16 mL, 2.0 eq), TEMPO (172 mg, 1.1 eq) and molecular sieve (120 mg, 4A, powder, pre-dried) was added CH₂Cl₂ (10 mL), which was then stirred for 1 h at room temperature under nitrogen gas. The reaction mixture was exposed to air, and stirred for one day. Saturated ammonium acetate (30 mL) was added thereto, and the mixture was extracted twice with ethyl acetate (100 mL). The extract was washed with dilute solution of sodium hydrogen carbonate (NaHCO₃, 100 mL×2), dried (anhydrous Na₂SO₄), and concentrated under reduced pressure. The residue was separated by column chromatography (20-35% ethyl acetate-hexane) to give 258 mg of the title compound in a stoichiometric yield.

¹H-NMR (500 MHz, CDCl₃) δ 7.75 (s, 1H), 7.58 (d, 2H), 7.44 (t, 2H), 7.36 (t, 1H), 3.70 (s, 3H), 3.68 (s, 2H), 2.25 (s, 3H)

Preparation 1-4)

2-(5-Methyl-3-oxo-2-phenyl-2,3-dihydro-pyridazin-4-yl)-butyric acid methyl ester The compound of Preparation 1-3) (258 mg, 1.0 mmol) was dissolved in anhydrous THF (10 mL) under nitrogen atmosphere and maintained at a temperature of −78° C. 1.0M LiHMDS/THF (1.20 mL, 1.2 eq) was added thereto, and the mixture was stirred for 10 min. Ethyl iodide (0.12 mL, 1.5 eq) was added, and the mixture was slowly warmed to room temperature, with stirring overnight. Water (20 mL) was added, and the mixture was extracted with ethyl acetate (50 mL×2), washed with aqueous sodium chloride solution (100 mL), dried (anhydrous Na₂SO₄), and concentrated under reduced pressure to give 286 mg of the title compound in a stoichiometric yield. This compound was used in the next reaction without further purification.

¹H-NMR (500 MHz, CDCl₃) δ 7.72 (s, 1H), 7.60 (d, 2H), 7.44 (t, 2H), 7.35 (t, 1H), 3.77 (dd, 1H), 3.70 (s, 3H), 2.28 (m, 1H), 2.26 (s, 3H), 1.90 (m, 1H), 0.92 (t, 3H)

Preparation 1-5)

2-(5-Methyl-3-oxo-2-phenyl-2,3-dihydro-pyridazin-4-yl)-butyric acid

The compound of Preparation 1-4) (286 mg) was dissolved in a solvent mixture (6 mL, tetrahydrofuran:MeOH:H₂O=3:2:1), LiOH.H₂O (126 mg, 3.0 eq) was added thereto, and the mixture was heated for about 2 h with stirring. The reaction solution was neutralized by 1N aqueous hydrochloric acid solution, and distilled under reduced pressure to almost thoroughly remove tetrahydrofuran. The residue was dissolved in excess ethyl acetate (50 mL), washed with aqueous sodium chloride solution, dried (anhydrous Na₂SO₄), and concentrated under reduced pressure to give the title compound (272 mg) in a stoichiometric yield. This compound was used in the next reaction without further purification.

Preparation 1-6)

5-Fluoro-3-[2-(5-methyl-3-oxo-2-phenyl-2,3-dihydro-pyridazin-4-yl)-butyryla mino]-4-oxo-pentanoic acid tert-butyl ester A mixture of the carboxylic acid derivative of Preparation 1-5) (271 mg, 1.00 mmol), 3-amino-5-fluoro-4-hydroxy-pentanoic acid tert-butyl ester (see *Tetrahedron Letters*, 1994, 35(52), 9693-9696, 248 mg, 1.2 eq) and HATU (494 mg, 1.3 eq) was cooled to 0° C., triethylamine (0.56 mL, 4.0 eq) was added thereto in DMF solvent (5 mL), and the mixture was reacted for one day. The solvent was distilled under reduced pressure. The residue was extracted with ethyl acetate (30 mL×2), washed with water, aqueous sodium hydrogen carbonate solution and aqueous sodium chloride solution, dried (anhydrous Na₂SO₄), and concentrated under reduced pressure. To this compound and Dess-Martin reagent (848 mg, 2.0 eq) was added anhydrous dichloromethane (4 mL), which was then stirred for 1 h at room temperature. The reaction was stopped by isopropyl alcohol (1 mL). The solid was removed by celite filtration under reduced pressure, and extracted with ethyl acetate (20 mL×2). The extract was washed with water, saturated aqueous sodium hydrogen carbonate solution and aqueous sodium chloride solution, dried (anhydrous Na₂SO₄), and concentrated under reduced pressure. The residue was separated by column chromatography (30-40% ethyl acetate-hexane) to give 330 mg (72%) of the title compound.

¹H-NMR (500 MHz, CDCl₃) δ 7.79 (br m, 1H), 7.62 (m, 1H), 7.50-7.25 (m, 5H), 5.20-4.80 (m, 2H), 4.80-4.68 (m, 1H), 3.75 (m, 1H), 2.88-2.57 (m, 2H), 2.26 (s, 3H), 2.26-1.98 (m, 2H), 1.41 (m, 9H), 0.87 (m, 3H)

Example 1)

5-Fluoro-3-[2-(5-methyl-3-oxo-2-phenyl-2,3-dihydro-pyridazin-4-yl)-butyryla mino]-4-oxo-pentanoic acid

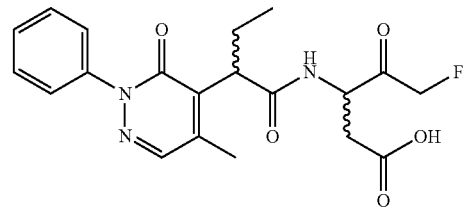 [SMILES: CCC(C(=O)NC(CC(=O)O)C(=O)CF)c1c(C)cnn(-c2ccccc2)c1=O]

The compound of Preparation 1-6) (100 mg, 0.218 mmol) was dissolved in dichloromethane (4 mL), and trifluoroacetic acid (2 mL) was added at 0° C. The mixture was stirred for 1 h, during which it was slowly warmed to room temperature. The mixture was concentrated under reduced pressure, and separated by column chromatography (10% methanol-dichloromethane) to give 68 mg (78%) of the title compound.

¹H-NMR (500 MHz, DMSO-d₆) δ 7.93 (m, 1H), 7.84 (br s, 1H), 7.45-7.37 (m, 5H), 5.03 (m, 2H), 4.57-4.49 (m, 1H), 3.69 (m, 1H), 2.68-2.47 (m, 2H), 2.19 (s, 3H), 2.08-1.68 (m, 2H), 0.76 (m, 3H)

Mass M+H⁺402.74

Preparation 2-1)

(2-Benzyl-5-methyl-3-oxo-2,3-dihydro-pyridazin-4-yl)-acetic acid methyl ester

To a mixture of the compound of Preparation 1-2) (364 mg, 2.0 mmol) and Cs₂CO₃ (977 mg, 1.5 eq) were added DMF (8 mL) and benzyl bromide (0.31 mL, 1.3 eq), which was then stirred for 3 h at 60° C. under nitrogen atmosphere. The mixture was concentrated under reduced pressure, and the residue was extracted twice with ethyl acetate (100 mL). The extract was washed with saturated aqueous sodium hydrogen carbonate solution (NaHCO₃, 100 mL×2) and aqueous sodium chloride solution, dried (anhydrous Na₂SO₄), and concentrated under reduced pressure. The residue was separated by column chromatography (30% ethyl acetate-hexane) to give 484 mg (89%) of the title compound.

$^1$H-NMR (500 MHz, CDCl$_3$) δ 7.61 (s, 1H), 7.39 (d, 2H), 7.35-7.26 (m, 3H), 5.29 (s, 2H), 3.70 (s, 3H), 3.65 (s, 2H), 2.15 (s, 3H)

Preparation 2-2)

2-(2-Benzyl-5-methyl-3-oxo-2,3-dihydro-pyridazin-4-yl)-butyric acid methyl ester The compound of Preparation 2-1) (471 mg, 1.73 mmol) was dissolved in anhydrous THF (6 mL) under nitrogen atmosphere, and maintained at −78° C. 1.0M LiHMDS/THF (2.10 mL, 1.2 eq) was added thereto, and the mixture was stirred for 10 min. Ethyl iodide (0.21 mL, 1.5 eq) was added, and the mixture was slowly warmed to room temperature with stirring overnight. The reaction was stopped by saturated ammonium acetate solution. The reaction mixture was extracted with ethyl acetate (50 mL×2), washed with aqueous sodium chloride solution (100 mL), dried (anhydrous Na$_2$SO$_4$), and concentrated under reduced pressure. The residue was separated by column chromatography (20% ethyl acetate-hexane) to give 400 mg (77%) of the title compound.

$^1$H-NMR (500 MHz, CDCl$_3$) δ 7.57 (s, 1H), 7.37 (d, 2H), 7.30-7.25 (m, 3H), 5.38 & 5.17 (two d, J=13.5 Hz, 2H), 3.70 (s, 3H), 3.69 (dd, 1H), 2.25 (m, 1H), 2.17 (s, 3H), 1.84 (m, 1H), 0.87 (t, 3H)

Preparation 2-3)

2-(2-Benzyl-5-methyl-3-oxo-2,3-dihydro-pyridazin-4-yl)-butyric acid

The compound of Preparation 2-2) (400 mg, 1.31 mmol) was dissolved in a solvent mixture (6 mL, tetrahydrofuran:MeOH:H$_2$O=3:2:1), LiOH.H$_2$O (165 mg, 3.0 eq) was added thereto, and the mixture was heated for about 2 h while stirring. The reaction mixture was neutralized by 1N aqueous hydrochloric acid solution, distilled under reduced pressure to almost thoroughly remove tetrahydrofuran. The residue was dissolved in excess ethyl acetate (50 mL), washed with aqueous sodium chloride solution, dried (anhydrous Na$_2$SO$_4$), and concentrated under reduced pressure to give 356 mg (Yield 100%) of the title compound. This compound was used in the next reaction without further purification.

Preparation 2-4)

3-[2-(2-Benzyl-5-methyl-3-oxo-2,3-dihydro-pyridazin-4-yl)-butyrylamino]-5-fluoro-4-oxo-pentanoic acid tert-butyl ester A mixture of the carboxylic acid derivative of Preparation 2-3) (153 mg, 0.535 mmol), 3-amino-5-fluoro-4-hydroxy-pentanoic acid tert-butyl ester (see *Tetrahedron Letters*, 1994, 35(52), 9693-9696, 133 mg, 1.2 eq) and HATU (265 mg, 1.3 eq) was cooled to 0° C., triethylamine (0.30 mL, 4.0 eq) was added thereto in DMF solvent (5 mL), and the mixture was reacted for one day. The solvent was distilled under reduced pressure. The residue was extracted with ethyl acetate (30 mL×2), washed with water, aqueous sodium hydrogen carbonate solution and aqueous sodium chloride solution, dried (anhydrous Na$_2$SO$_4$), and concentrated under reduced pressure. The residue was separated by column chromatography (40-60% ethyl acetate-hexane) to give 233 mg (92%) of 3-[2-(2-benzyl-5-methyl-3-oxo-2,3-dihydro-pyridazin-4-yl)butyrylamino]-5-fluoro-4-hydroxy-pentanoic acid tert-butyl ester. To this compound and Dess-Martin reagent (312 mg, 3.0 eq) was added anhydrous dichloromethane (4 mL), which was then stirred for 1 h at room temperature. The reaction was stopped by isopropyl alcohol (1 mL). The solid was removed by celite filtration under reduced pressure, and extracted with ethyl acetate (20 mL×2). The extract was washed with water, saturated aqueous sodium hydrogen carbonate solution and aqueous sodium chloride solution, dried (anhydrous Na$_2$SO$_4$), and concentrated under reduced pressure. The residue was separated by column chromatography (30-40% ethyl acetate-hexane) to give 201 mg (79%) of the title compound.

$^1$H-NMR (500 MHz, CDCl$_3$) δ 8.13 (br s, 1H), 7.62 (s, 1H), 7.38-7.25 (m, 5H), 5.38-5.20 (m, 2H), 5.20-4.80 (m, 2H), 4.80-4.68 (m, 1H), 3.76 (m, 1H), 2.88-2.57 (m, 2H), 2.26 (s, 3H), 2.26-1.98 (m, 2H), 1.41 (m, 9H), 0.87 (m, 3H)

Example 2)

3-[2-(2-Benzyl-5-methyl-3-oxo-2,3-dihydro-pyridazin-4-yl)-butyrylamino]-5-fluoro-4-oxo-pentanoic acid

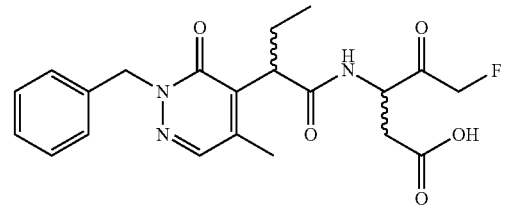 [SMILES: CCC(C(=O)NC(CC(=O)O)C(=O)CF)c1c(C)cnn(Cc2ccccc2)c1=O]

The compound of Preparation 2-4) (198 mg, 0.418 mmol) was dissolved in dichloromethane (4 mL), and trifluoroacetic acid (2 mL) was added at 0° C. The mixture was stirred for 1 h, during which it was slowly warmed to room temperature. The mixture was concentrated under reduced pressure, and separated by column chromatography (10% methanol-dichloromethane) to give 175 mg (stoichiometric yield, white powder) of the title compound.

$^1$H-NMR (500 MHz, DMSO-d$_6$) δ 12.31 (br s, 1H), 7.95-7.86 (dd, 1H), 7.79 (s, 1H), 7.28-7.22 (m, 5H), 5.34-4.86 (m, 4H), 4.49-4.39 (m, 1H), 3.60 (m, 1H), 2.70-2.35 (m, 2H), 2.14 (s, 3H), 2.05-1.68 (m, 2H), 0.70 (m, 3H)

Preparation 3-1)

2-Benzyl-4,5-dichloro-2H-pyridazin-3-one

To a mixture of 4,5-dichloro-2H-pyridazin-3-one (3.3 g, 20.0 mmol) and Cs$_2$CO$_3$ (9.77 mg, 1.5 eq) were added DMF (15 mL) and benzyl bromide (3.10 mL, 1.3 eq), which was then stirred for 3 h at 60° C. under nitrogen atmosphere. The mixture was concentrated under reduced pressure, and the residue was extracted twice with ethyl acetate (200 mL). The extract was washed with saturated aqueous sodium hydrogen carbonate solution (NaHCO$_3$, 100 mL×2) and aqueous sodium chloride solution, dried (anhydrous Na$_2$SO$_4$), and concentrated under reduced pressure. The residue was separated by column chromatography (10% ethyl acetate-hexane) to give 4.48 g (88%) of the title compound.

$^1$H-NMR (500 MHz, CDCl$_3$) δ 7.77 (s, 1H), 7.43 (d, 2H), 7.35-7.30 (m, 3H), 5.32 (s, 2H)

Preparation 3-2)

(2-Benzyl-5-chloro-3-oxo-2,3-dihydro-pyridazin-4-yl)-acetic acid ethyl ester

Diethylmalonate (1.73 g, 1.64 mL, 2.5 eq) was dissolved in isopropyl ether (2 mL), sodium ethoxide (0.73 g, 2.5 eq) was added thereto at room temperature, and the mixture was stirred for 30 min. To the reaction mixture was added the compound of Preparation 3-1) (1.10 g, 4.31 mmol), which was then refluxed for one day. The mixture was extracted with ethyl acetate (50 mL×2), washed with aqueous sodium chloride solution (100 mL), dried (anhydrous $Na_2SO_4$), and concentrated under reduced pressure. The residue was separated by column chromatography (10-20% ethyl acetate-hexane) to give 1.34 g (82%) of a 1:1 mixture of 2-(2-benzyl-5-chloro-3-oxo-2,3-dihydro-pyridazin-4-yl)-malonic acid diethyl ester and 2-(1-benzyl-5-chloro-6-oxo-1,6-dihydro-pyridazin-4-yl)-malonic acid diethyl ester. This mixture was dissolved in 12 mL of a solvent mixture ($H_2O$:DMSO=1:5), NaCl (1.0 g, 5 eq) was added thereto, and the mixture was heated to 120° C. for one day. The mixture was concentrated under reduced pressure, and the residue was extracted twice with ethyl acetate (200 mL). The extract was washed with water, saturated sodium hydrogen carbonate solution ($NaHCO_3$, 100 mL×2) and aqueous sodium chloride solution, dried (anhydrous $Na_2SO_4$), and concentrated under reduced pressure. The residue was separated by column chromatography (10-20% ethyl acetate-hexane) to give 530 mg (49%) of the title compound.

$^1$H-NMR (500 MHz, $CDCl_3$) δ 7.76 (s, 1H), 7.39 (d, 2H), 7.33-7.26 (m, 3H), 5.29 (s, 2H), 4.17 (qt, 2H), 3.75 (s, 2H), 1.24 (t, 3H)

Preparation 3-3)

(2-Benzyl-3-oxo-2,3-dihydro-pyridazin-4-yl)-acetic acid ethyl ester

The compound of Preparation 3-2) (1.15 g, 3.75 mmol) was dissolved in 30 mL of EtOH, 10% Pd/C (200 mg, Aldrich) was added, and the mixture was stirred for 3 h under hydrogen atmosphere. The reaction mixture was passed through celite, washed twice with ethanol, and the ethanol extract was concentrated under reduced pressure to give 1.00 g (98%) of the title compound.

$^1$H-NMR (500 MHz, $CDCl_3$) δ 7.74 (d, 1H), 7.42 (d, 2H), 7.33-7.26 (m, 3H), 7.17 (d, 1H), 5.33 (s, 2H), 4.18 (qt, 2H), 3.59 (s, 2H), 1.25 (t, 3H)

Preparation 3-4)

2-(2-Benzyl-3-oxo-2,3-dihydro-pyridazin-4-yl)-butyric acid ethyl ester

The compound of Preparation 3-3) (272 mg, 1.00 mmol) was dissolved in anhydrous THF (5 mL) under nitrogen atmosphere and maintained at a temperature of −78° C. 1.0M LiHMDS/THF (1.50 mL, 1.5 eq) was added thereto, and the mixture was stirred for 10 min. Ethyl iodide (0.14 mL, 1.8 eq) was added, and the mixture was slowly warmed to room temperature, with stirring overnight. The reaction was stopped by saturated ammonium acetate solution. The reaction mixture was extracted with ethyl acetate (50 mL×2), washed with aqueous sodium chloride solution (100 mL), dried (anhydrous $Na_2SO_4$), and concentrated under reduced pressure. The residue was separated by column chromatography (10-20% ethyl acetate-hexane) to give 220 mg (73%, oil) of the title compound.

$^1$H-NMR (500 MHz, $CDCl_3$) δ 7.74 (d, 1H), 7.42 (d, 2H), 7.33-7.26 (m, 3H), 7.17 (d, 1H), 5.32 (ABq, 2H), 4.18-4.10 (m, 2H), 3.87 (t, 2H), 2.01-1.77 (m, 2H), 1.21 (t, 3H), 0.95 (t, 3H)

Preparation 3-5)

3-[2-(2-Benzyl-3-oxo-2,3-dihydro-pyridazin-4-yl)-butyrylamino]-5-fluoro-4-oxo-pentanoic acid tert-butyl ester The compound of Preparation 3-4) was hydrolyzed according to the same procedure as Preparation 2-3) to give carboxylic acid derivative. A mixture of this carboxylic acid derivative (205 mg, 0.683 mmol), 3-amino-5-fluoro-4-hydroxy-pentanoic acid tert-butyl ester (see *Tetrahedron Letters*, 1994, 35(52), 9693-9696, 170 mg, 1.2 eq) and HATU (337 mg, 1.3 eq) was cooled to 0° C., triethylamine (0.38 mL, 4.0 eq) was added thereto in DMF solvent (5 mL), and the mixture was reacted for one day. The solvent was distilled under reduced pressure. The residue was extracted with ethyl acetate (30 mL×2), washed with water, aqueous sodium hydrogen carbonate solution and aqueous sodium chloride solution, dried (anhydrous $Na_2SO_4$), and concentrated under reduced pressure to give 3-[2-(2-benzyl-3-oxo-2,3-dihydro-pyridazin-4-yl)butyrylamino]-5-fluoro-4-hydroxy-pentanoic acid tert-butyl ester. To this compound and Dess-Martin reagent (580 mg, 2.0 eq) was added anhydrous dichloromethane (4 mL), which was then stirred for 1 h at room temperature. The reaction was stopped by isopropyl alcohol (1 mL). The solid was removed by celite filtration under reduced pressure, and extracted with ethyl acetate (20 mL×2). The extract was washed with water, saturated aqueous sodium hydrogen carbonate solution and aqueous sodium chloride solution, dried (anhydrous $Na_2SO_4$), and concentrated under reduced pressure. The residue was separated by column chromatography (20-30% ethyl acetate-hexane) to give 242 mg (77%) of the title compound.

$^1$H-NMR (500 MHz, $CDCl_3$) δ 7.79 (m, 1H), 7.56 (m, 1H), 7.42-7.27 (m, 5H), 7.14 (m, 1H), 5.40-5.27 (m, 2H), 5.22-4.67 (m, 3H), 3.76 (m, 1H), 2.93-2.56 (m, 2H), 2.16 (m, 1H), 1.69 (m, 1H), 1.42 & 1.38 (two s, 9H), 0.95 (m, 3H)

Example 3)

3-[2-(2-Benzyl-3-oxo-2,3-dihydro-pyridazin-4-yl)-butyrylamino]-5-fluoro-4-oxo-pentanoic acid

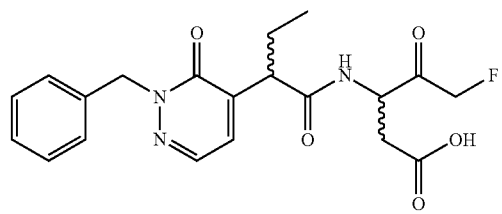 [SMILES: CCC(C(=O)NC(CC(=O)O)C(=O)CF)c1ccnn(Cc2ccccc2)c1=O]

The compound of Preparation 3-5) (242 mg, 0.527 mmol) was reacted according to the same procedure as Example 2) to give 195 mg (92%) of the title compound.

$^1$H-NMR (500 MHz, DMSO-$d_6$) δ 12.40 (br s, 1H), 8.70 (m, 1H), 7.87 (m, 1H), 7.27-7.24 (m, 6H), 5.25-5.16 (m, 2H), 5.21 (m, 2H), 4.58-4.47 (m, 1H), 3.64 (m, 1H), 2.69-2.47 (m, 2H), 1.72-1.62 (m, 2H), 0.82 (m, 3H)

Preparation 4-1)

2-(2-Benzyl-5-chloro-3-oxo-2,3-dihydro-pyridazin-4-yl)-butyric acid ethyl ester

The compound of Preparation 3-2) (170 mg, 0.554 mmol) was reacted according to the same procedure as Preparation 3-4) to give 137 mg (74%) of the title compound.

$^1$H-NMR (500 MHz, CDCl$_3$) δ 7.74 (s, 1H), 7.38-7.26 (m, 5H), 5.37-5.17 (ABq, 2H), 4.18-4.02 (m, 2H), 3.91 (dd, 1H), 2.27 (m, 1H), 1.90 (m, 1H), 1.08 (t, 3H), 0.89 (t, 3H)

Preparation 4-2)

2-(2-Benzyl-5-chloro-3-oxo-2,3-dihydro-pyridazin-4-yl)-butyric acid and 2-(2-Benzyl-5-methoxy-3-oxo-2,3-dihydro-pyridazin-4-yl)-butyric acid The compound of Preparation 4-1) (132 mg, 0.395 mmol) was dissolved in a solvent mixture (6 mL, tetrahydrofuran:MeOH:H$_2$O=3:2:1), LiOH.H$_2$O (50 mg, 3.0 eq) was added thereto, and the mixture was stirred for one day. The reaction mixture was neutralized by 1N aqueous hydrochloric acid solution, and distilled under reduced pressure to almost thoroughly remove tetrahydrofuran. The residue was dissolved in excess ethyl acetate (50 mL), washed with aqueous sodium chloride solution, dried (anhydrous Na$_2$SO$_4$), and concentrated under reduced pressure to give 118 mg of the title compound, which was then identified by NMR to be a mixture of the chloro derivative and the methoxy derivative in a ratio of 0.4:1.0. These compounds were used in the next reaction without further purification.

Preparation 4-3)

3-[2-(2-Benzyl-5-chloro-3-oxo-2,3-dihydro-pyridazin-4-yl)-butyrylamino]-5-fluoro-4-oxo-pentanoic acid tert-butyl ester and 3-[2-(2-Benzyl-5-methoxy-3-oxo-2,3-dihydro-pyridazin-4-yl)-butyrylamino]-5-fluoro-4-oxo-pentanoic acid tert-butyl ester The two compounds obtained in Preparation 4-2) were reacted according to the same procedure as Preparation 2-4), and were separated by column chromatography (30-50% ethyl acetate-hexane) to give the chloro derivative (45 mg, 23%) and the methoxy derivative (62 mg, 32%).

Chloro Derivative $^1$H-NMR (500 MHz, CDCl$_3$) δ 7.78 (s, 1H), 7.70 (m, 1H), 7.42-7.27 (m, 5H), 5.35-4.86 (m, 4H), 4.78-4.67 (m, 1H), 4.01 (m, 1H), 2.94-2.62 (m, 2H), 2.28-2.06 (m, 2H), 1.69 (m, 1H), 1.42 & 1.41 (two s, 9H), 0.89 (m, 3H)

Methoxy Derivative $^1$H-NMR (500 MHz, CDCl$_3$) δ 8.14-8.03 (br m, 1H), 7.84 (m, 1H), 7.40-7.26 (m, 5H), 5.40-4.70 (m, 5H), 3.94 (two s, 3H), 3.94 (m, 1H), 2.88-2.58 (m, 2H), 2.26-1.90 (m, 2H), 1.42 & 1.40 (two s, 9H), 0.86 (m, 3H)

Example 4)

3-[2-(2-Benzyl-5-chloro-3-oxo-2,3-dihydro-pyridazin-4-yl)-butyrylamino]-5-fluoro-4-oxo-pentanoic acid

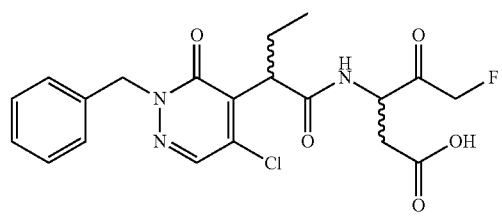

The chloro compound of Preparation 4-3) (45 mg, 0.091 mmol) was reacted according to the same procedure as Example 2) to give 23 mg (58%) of the title compound.

$^1$H-NMR (500 MHz, DMSO-d$_6$) δ 8.17 (s, 1H), 7.97 (m, 1H), 7.40-7.23 (m, 5H), 5.36-5.29 (m, 1H), 5.29-4.70 (m, 2H), 5.09-5.05 (m, 1H), 4.52-4.43 (m, 1H), 3.74 (m, 1H), 2.67-2.46 (m, 2H), 2.10-1.74 (m, 2H), 0.73 (m, 3H)

Example 5)

3-[2-(2-Benzyl-5-methoxy-3-oxo-2,3-dihydro-pyridazin-4-yl)-butyrylamino]-5-fluoro-4-oxo-pentanoic acid

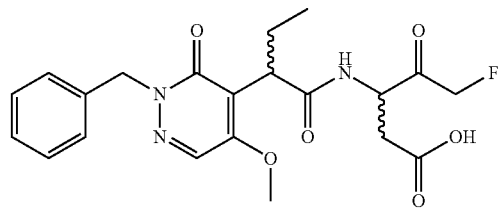 [SMILES: CCC(C(=O)NC(CC(=O)O)C(=O)CF)c1c(OC)cnn(Cc2ccccc2)c1=O]

The methoxy compound of Preparation 4-3) (62 mg, 0.127 mmol) was reacted according to the same procedure as Example 2) to give 28 mg (51%) of the title compound.

$^1$H-NMR (500 MHz, DMSO-d$_6$) δ 8.17 (s, 1H), 7.89-7.81 (m, 1H), 7.26-7.21 (m, 5H), 5.34-5.09 (Ab q, 2H), 5.29-4.70 (m, 2H), 4.52-4.40 (m, 1H), 3.90 (d, 3H), 3.62 (m, 1H), 2.65-2.46 (m, 2H), 1.97-1.64 (m, 2H), 0.68 (m, 3H)

Preparation 6-1)

4,5-Dichloro-2-methoxymethyl-2H-pyridazin-3-one 4,5-Dichloro-2H-pyridazin-3-one (30 g, 182 mmol), N,N-diisopropylethylamine (47.5 mL, 258 mmol) and 4-dimethylaminopyridine (2.20 g, 18.2 mmol) were dissolved in 200 mL of methylene chloride, to which was slowly added dropwise chloromethyl methyl ether (16.6 mL, 21.8 mmol) while maintaining at 0° C. The mixture was stirred for 3 h at room temperature. The reaction solution was washed with saturated aqueous sodium hydrogen carbonate solution, distilled under reduced pressure, and separated-purified by column chromatography (10% methylene chloride/ethyl acetate) to give the title compound (26.6 g, Yield: 70%) as a yellow solid.

$^1$H-NMR (CDCl$_3$, 400 MHz) δ 7.81 (s, 1H), 5.45 (s, 2H), 3.48 (s, 3H)

Preparation 6-2)

2-(5-Chloro-2-methoxymethyl-3-oxo-2,3-dihydro-pyridazin-4-yl)-malonic acid diethyl ester and 2-(5-chloro-1-methoxymethyl-6-oxo-1,6-dihydro-pyridazin-4-yl)-malonic acid diethyl ester The compound of Preparation 6-1) (26.6 g, 127 mmol) and sodium ethoxide (13 g, 191 mmol) were suspended in diisopropyl ether (100 mL), and stirred for 30 min. Diethyl malonate (29.0 mL, 191 mmol) was added thereto, and the mixture was refluxed for one day. After completion of the reaction, the mixture was distilled under reduced pressure to remove diisopropyl ether. The residue was dissolved again in methylene chloride, washed with 1N hydrochloric acid and saturated aqueous sodium hydrogen carbonate solution, and distilled under reduced pressure. The residue was separated by column chromatography (14.3%, ethyl acetate/hexane) to give the title mixture in a ratio of 1:1 (32 g, Yield: 76%) as a pale yellow liquid.

Preparation 6-3)

(5-Chloro-2-methoxymethyl-3-oxo-2,3-dihydro-pyridazin-4-yl)-acetic acid ethyl ester The compound of Preparation 6-2) (32.0 g, 96.2 mmol) and sodium chloride (228 g, 481 mmol) were dissolved in water/dimethylsulfoxide (120 mL, ⅕), and stirred for 16 h at 170° C. Dimethylsulfoxide was removed by distillation in vacuo. The residue was dissolved in methylene chloride, washed with water, distilled under reduced pressure, and separated by column chromatography (33%, ethyl acetate/hexane) to give the title compound (12 g, Yield: 48%) as a colorless liquid.

$^1$H-NMR (CDCl$_3$, 500 MHz) δ 7.78 (s, 1H), 5.42 (s, 2H), 4.18 (t, 2H), 3.77 (s, 2H), 3.44 (s, 3H), 1.26 (q, 3H)

Preparation 6-4)

(2-Methoxymethyl-3-oxo-2,3-dihydro-pyridazin-4-yl)-acetic acid ethyl ester

The compound of Preparation 6-3) (405 mg, 1.55 mmol) was dissolved in 10 mL of EtOH, 10% Pd/C (100 mg, Aldrich) was added, and the mixture was stirred for 1 h under hydrogen atmosphere. The reaction mixture was passed through celite, and washed twice with ethanol. The ethanol extract was concentrated under reduced pressure, and separated by column chromatography (40-50%, ethyl acetate/hexane) to give the title compound (240 mg, Yield: 68%) as a colorless liquid.

$^1$H-NMR (500 MHz, CDCl$_3$) δ 7.76 (d, 1H), 7.21 (d, 1H), 5.45 (s, 2H), 4.18 (qt, 2H), 3.45 (s, 3H), 1.27 (t, 3H)

Preparation 6-5)

2-(2-Methoxymethyl-3-oxo-2,3-dihydro-pyridazin-4-yl)-butyric acid ethyl ester

The compound of Preparation 6-4) (240 mg, 1.06 mmol) was reacted according to the same procedure as Preparation 2-2) to give 179 mg (67%) of the title compound.

$^1$H-NMR (500 MHz, CDCl$_3$) δ 7.77 (d, 1H), 7.21 (d, 1H), 5.46 (m, 2H), 4.22-4.10 (m, 2H), 3.88 (m, 1H), 3.45 (s, 3H), 2.00-1.78 (two m, 2H), 1.24 (t, 3H), 0.96 (t, 3H)

Preparation 6-6)

2-(3-Oxo-2,3-dihydro-pyridazin-4-yl)-butyric acid ethyl ester

The compound of Preparation 6-5) (172 mg, 0.676 mmol) was dissolved in 8 mL of CH$_2$Cl$_2$, BBr$_3$ (70 μl, or 1.1 eq/1.0M solution in CH$_2$Cl$_2$) was added at −78° C., and the mixture was stirred for 2 h while slowly warming to room temperature. The reaction was stopped by saturated ammonium acetate. The reaction mixture was extracted with ethyl acetate, and washed with aqueous sodium chloride solution. The extract was concentrated under reduced pressure, and separated by Prep-TLC (70%, ethyl acetate/hexane) to give the title compound (132 mg, Yield: 91%) as a colorless liquid.

$^1$H-NMR (500 MHz, CDCl$_3$) δ 7.76 (d, 1H), 7.26 (d, 1H), 4.18-4.10 (m, 2H), 3.88 (m, 1H), 2.00-1.75 (two m, 2H), 1.23 (t, 3H), 0.94 (t, 3H)

Preparation 6-7)

1-Bromomethyl-2-tert-butyl-benzene

To 1-tert-butyl-2-methyl-benzene (940 mg, 6.34 mmol), NBS (1.24 g, 1.1 eq) and AIBN (20 mg, catalytic amount) was added CCl$_4$ (12 mL), which was then refluxed for 1 h. The suspended particles were removed by filtration, and washed with CCl$_4$. The organic layers were combined and concentrated under reduced pressure to give 1.5 g of a yellow liquid in a stoichiometric yield.

$^1$H-NMR (500 MHz, CDCl$_3$) δ 7.46 (m, 1H), 7.38 (m, 1H), 7.22-7.21 (m, 2H), 4.83 (s, 2H), 1.46 (s, 9H)

Preparation 6-8)

2-[2-(2-tert-Butyl-benzyl)-3-oxo-2,3-dihydro-pyridazin-4-yl]-butyric acid ethyl ester The compound of Preparation 6-6) (58 mg, 0.276 mmol) and the compound of Preparation 6-7) (81 mg, 1.3 eq) were reacted according to the same procedure as Preparation 2-1) to give 53 mg (54%) of the title compound.

$^1$H-NMR (500 MHz, CDCl$_3$) δ 7.78 (d, 1H), 7.42 (d, 1H), 7.25 (m, 1H), 7.18 (d, 1H), 7.09 (t, 1H), 6.82 (d, 1H), 5.66 (ABq, 2H), 4.21-4.10 (m, 2H), 3.94 (t, 1H), 2.03-1.80 (two m, 2H), 1.49 (s, 9H), 1.23 (t, 3H), 0.97 (t, 3H)

Preparation 6-9)

3-2-[2-(2-tert-Butyl-benzyl)-3-oxo-2,3-dihydro-pyridazin-4-yl]-butyrylamino-5-fluoro-4-oxo-pentanoic acid tert-butyl ester The compound of Preparation 6-8) (53 mg, 0.149 mmol) was reacted according to the same procedure as Preparation 3-5) to give 46 mg (60%) of the title compound.

$^1$H-NMR (500 MHz, CDCl$_3$) δ 7.84 (two d, 1H), 7.52 (m, 1H), 7.43 (two s, 1H), 7.23-7.09 (m, 2H), 7.08 (two d, 1H), 5.71 & 5.66 (two s, 2H), 5.21-4.70 (m, 3H), 3.81 (m, 1H), 2.91-2.58 (m, 2H), 2.17 (m, 1H), 1.72 (m, 1H), 1.50 (s, 9H), 1.40 & 1.36 (two s, 9H), 0.97 (m, 3H)

Example 6)

3-2-[2-(2-tert-Butyl-benzyl)-3-oxo-2,3-dihydro-pyridazin-4-yl]-butyrylamino-5-fluoro-4-oxo-pentanoic acid

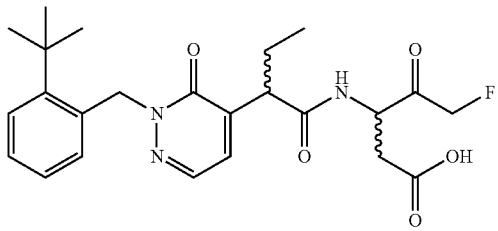 [SMILES: CCC(C(=O)NC(CC(=O)O)C(=O)CF)c1ccnn(Cc2ccccc2C(C)(C)C)c1=O]

The compound of Preparation 6-9) (46 mg, 0.089 mmol) was reacted according to the same procedure as Example 2) to give the title compound (29 mg, 71%).
$^1$H-NMR (500 MHz, DMSO-$d_6$) δ 8.65-8.61 (m, 1H), 7.93 (q, 1H), 7.39-7.34 (m, 2H), 7.14 (t, 1H), 7.04 (t, 1H), 6.67 (m, 1H), 5.50 (Ab q, 2H), 5.02 (m, 2H), 4.58-4.48 (m, 1H), 3.69 (m, 1H), 2.63 (m, 2H), 1.75-1.64 (m, 2H), 1.40 (s, 9H), 0.83 (m, 3H)

Preparation 7-1)

1-Bromomethyl-3-tert-butyl-benzene

To 1-methyl-3-tert-butyl-benzene (551 mg, 3.72 mmol), NBS (730 mg, 1.1 eq) and AIBN (14 mg, catalytic amount) was added $CCl_4$ (8 mL), which was then refluxed for 2 h. The suspended particles were removed by filtration, and washed with $CCl_4$. The organic layers were combined and concentrated under reduced pressure to give 860 mg of a yellow liquid (which was identified by NMR to contain about 15% dibromo derivative).
$^1$H-NMR (500 MHz, CDCl$_3$) δ 7.39-7.19 (m, 4H), 4.51 (s, 2H), 1.35 (s, 9H)

Preparation 7-2)

2-[2-(3-tert-Butyl-benzyl)-3-oxo-2,3-dihydro-pyridazin-4-yl]-butyric acid ethyl ester To a mixture of the compound of Preparation 6-6) (50 mg, 0.238 mmol) and $Cs_2CO_3$ (116 mg, 1.5 eq) were added DMF (3 mL) and 1-bromomethyl-3-tert-butyl-benzene of Preparation 7-1) (70 mg, 1.3 eq), which was then stirred for 2 h at 60° C. under nitrogen atmosphere. The mixture was concentrated under reduced pressure, and the residue was extracted twice with ethyl acetate (50 mL). The extract was washed with saturated aqueous sodium hydrogen carbonate solution ($NaHCO_3$, mL×2) and aqueous sodium chloride solution, dried (anhydrous $Na_2SO_4$), and concentrated under reduced pressure. The residue was separated by Prep-TLC (30% ethyl acetate-hexane) to give 57 mg (67%) of the title compound.
$^1$H-NMR (500 MHz, CDCl$_3$) δ 7.74 (d, 1H), 7.43 (s, 1H), 7.30-7.16 (m, 4H), 5.32 (ABq, 2H), 4.18-4.10 (m, 2H), 3.88 (t, 1H), 1.99-1.76 (two m, 2H), 1.29 (s, 9H), 1.20 (t, 3H), 0.95 (t, 3H)

Preparation 7-3)

3-2-[2-(3-tert-Butyl-benzyl)-3-oxo-2,3-dihydro-pyridazin-4-yl]-butyrylamino-5-fluoro-4-oxo-pentanoic acid tert-butyl ester The compound of Preparation 7-2) (56 mg, 0.157 mmol) was reacted according to the same procedure as Preparation 3-5) to give the title compound (49 mg, 60%).

$^1$H-NMR (500 MHz, CDCl$_3$) δ 7.79 (two d, 1H), 7.58 (m, 1H), 7.42 (two s, 1H), 7.32-7.14 (m, 4H), 5.35-5.28 (m, 2H), 5.21-4.68 (m, 3H), 3.75 (m, 1H), 2.91-2.58 (m, 2H), 2.14 (m, 1H), 1.69 (m, 1H), 1.43 & 1.41 (two s, 9H), 1.29 (s, 9H), 0.95 (m, 3H)

Example 7)

3-2-[2-(3-tert-Butyl-benzyl)-3-oxo-2,3-dihydro-pyridazin-4-yl]-butyrylamino-5-fluoro-4-oxo-pentanoic acid

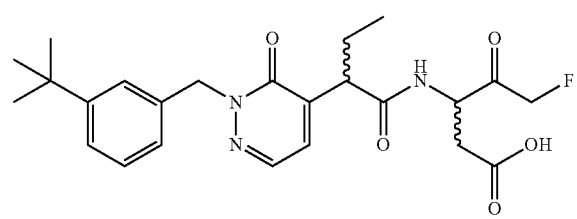 [SMILES: CCC(C(=O)NC(CC(=O)O)C(=O)CF)c1ccnn(Cc2cccc(C(C)(C)C)c2)c1=O]

The compound of Preparation 7-3) (48 mg, 0.0931 mmol) was reacted according to the same procedure as Example 2) to give the title compound (31 mg, 72%).
$^1$H-NMR (500 MHz, DMSO-$d_6$) δ 8.65 (m, 1H), 7.89 (q, 1H), 7.31 (t, 1H), 7.27 (s, 1H), 7.26 (m, 1H), 7.19 (t, 1H), 7.00 (m, 1H), 5.21 (m, 2H), 5.20-4.67 (m, 2H), 4.57-4.48 (m, 1H), 3.68 (m, 1H), 2.62 (m, 2H), 1.73-1.63 (m, 2H), 1.20 (s, 9H), 0.83 (m, 3H)

Preparation 8-1)

2-[2-(2-Methyl-benzyl)-3-oxo-2,3-dihydro-pyridazin-4-yl]-butyric acid ethyl ester The compound of Preparation 6-6) (98 mg, 0.47 mmol) and 1-bromomethyl-2-methylbenzene (112 mg, 1.3 eq) were reacted according to the same procedure as Preparation 2-1) to give the title compound (118 mg, 80%).
$^1$H-NMR (500 MHz, CDCl$_3$) δ 7.75 (d, 1H), 7.20-7.13 (m, 5H), 5.40-5.31 (ABq, 2H), 4.20-4.10 (m, 2H), 3.89 (m, 1H), 2.40 (s, 3H), 1.97 (m, 1H), 1.82 (m, 1H), 1.22 (t, 3H), 0.96 (t, 3H)

Preparation 8-2)

5-Fluoro-3-2-[2-(2-methyl-benzyl)-3-oxo-2,3-dihydro-pyridazin-4-yl]-butyryl amino-4-oxo-pentanoic acid tert-butyl ester The compound of Preparation 8-1) (118 mg, 0.38 mmol) was reacted according to the same procedure as Preparation 3-5) to give the title compound (145 mg, 82%).
$^1$H-NMR (500 MHz, CDCl$_3$) δ 7.80 (two d, 1H), 7.57 (m, 1H), 7.20-7.13 (m, 5H), 5.38-5.35 (two s, 2H), 5.21-4.68 (m, 3H), 3.77 (m, 1H), 2.91-2.57 (m, 2H), 2.42 & 2.41 (two s, 3H), 2.15 (m, 1H), 1.70 (m, 1H), 1.43 & 1.39 (two s, 9H), 0.95 (m, 3H)

Example 8)

5-Fluoro-3-2-[2-(2-methyl-benzyl)-3-oxo-2,3-dihydro-pyridazin-4-yl]-butyryl amino-4-oxo-pentanoic acid

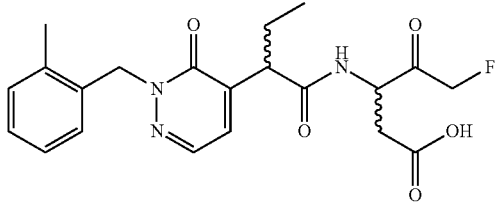 [SMILES: CCC(C(=O)NC(CC(=O)O)C(=O)CF)c1ccnn(Cc2ccccc2C)c1=O]

The compound of Preparation 8-2) (143 mg, 0.302 mmol) was reacted according to the same procedure as Example 2) to give the title compound (109 mg, 87%).

$^1$H-NMR (500 MHz, DMSO-d$_6$) δ 12.40 (br s, 1H), 8.72-8.63 (m, 1H), 7.88 (m, 1H), 7.31 (m, 1H), 7.14 (m, 2H), 7.07 (t, 1H), 6.94 (t, 1H), 5.28-4.95 (m, 4H), 4.58-4.48 (m, 1H), 3.65 (m, 1H), 2.69-2.47 (m, 2H), 2.29 (s, 3H), 1.73-1.64 (m, 2H), 0.83 (m, 3H)

Preparation 9-1)

2-[2-(3-Methyl-benzyl)-3-oxo-2,3-dihydro-pyridazin-4-yl]-butyric acid ethyl ester The compound of Preparation 6-6) (103 mg, 0.49 mmol) and 1-bromomethyl-3-methylbenzene (118 mg, 1.3 eq) were reacted according to the same procedure as Preparation 2-1) to give the title compound (110 mg, 71%).

$^1$H-NMR (500 MHz, CDCl$_3$) δ 7.74 (d, 1H), 7.22-7.08 (m, 4H), 7.08 (m, 1H), 5.33-5.24 (ABq, 2H), 4.20-4.01 (m, 2H), 3.88 (m, 1H), 2.32 (s, 3H), 1.95 (m, 1H), 1.81 (m, 1H), 1.21 (t, 3H), 0.95 (t, 3H)

Preparation 9-2)

5-Fluoro-3-2-[2-(3-methyl-benzyl)-3-oxo-2,3-dihydro-pyridazin-4-yl]-butyryl amino-4-oxo-pentanoic acid tert-butyl ester The compound of Preparation 9-1) (110 mg, 0.35 mmol) was reacted according to the same procedure as Preparation 3-5) to give the title compound (141 mg, 89%).

$^1$H-NMR (500 MHz, CDCl$_3$) δ 7.79 (two d, 1H), 7.59 (m, 1H), 7.22-7.08 (m, 5H), 5.36-4.69 (m, 5H), 3.75 (m, 1H), 2.92-2.59 (m, 2H), 2.32 (two s, 3H), 2.15 (m, 1H), 1.70 (m, 1H), 1.44 & 1.41 (two s, 9H), 0.95 (m, 3H)

Example 9)

5-Fluoro-3-2-[2-(3-methyl-benzyl)-3-oxo-2,3-dihydro-pyridazin-4-yl]-butyryl amino-4-oxo-pentanoic acid

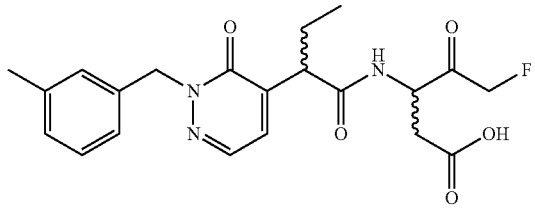 [SMILES: CCC(C(=O)NC(CC(=O)O)C(=O)CF)c1ccnn(Cc2cccc(C)c2)c1=O]

The compound of Preparation 9-2) (137 mg, 0.289 mmol) was reacted according to the same procedure as Example 2) to give the title compound (104 mg, 86%).

$^1$H-NMR (500 MHz, DMSO-d$_6$) δ 12.41 (br s, 1H), 8.72-8.64 (m, 1H), 7.87 (m, 1H), 7.29 (s, 1H), 7.16 (t, 1H), 7.05 (m, 3H), 5.26-4.92 (m, 4H), 4.58-4.47 (m, 1H), 3.66 (m, 1H), 2.69-2.47 (m, 2H), 2.22 (s, 3H), 1.73-1.63 (m, 2H), 0.83 (m, 3H)

Preparation 10-1)

2-[2-(3-Methoxy-benzyl)-3-oxo-2,3-dihydro-pyridazin-4-yl]-butyric acid ethyl ester The compound of Preparation 6-6) (114 mg, 0.54 mmol) and 1-bromomethyl-3-methoxy-benzene (142 mg, 1.3 eq) were reacted according to the same procedure as Preparation 2-1) to give the title compound (145 mg, 81%).

$^1$H-NMR (400 MHz, CDCl$_3$) δ 7.79 (d, 1H), 7.25 (t, 1H), 7.22 (d, 1H), 7.03 (d, 1H), 7.00 (s, 1H), 6.87 (d, 1H), 5.40-5.30 (ABq, 2H), 4.21-4.13 (m, 2H), 3.93 (t, 1H), 3.82 (s, 3H), 1.98 (m, 1H), 1.85 (m, 1H), 1.26 (t, 3H), 1.00 (t, 3H)

Preparation 10-2)

5-Fluoro-3-2-[2-(3-methoxy-benzyl)-3-oxo-2,3-dihydro-pyridazin-4-yl]-butyr ylamino-4-oxo-pentanoic acid tert-butyl ester The compound of Preparation 10-1) (145 mg, 0.44 mol) was reacted according to the same procedure as Preparation 3-5) to give the title compound (70 mg, 33%).

$^1$H-NMR (500 MHz, CDCl$_3$) δ 7.79 (two d, 1H), 7.58 (m, 1H), 7.23 (t, 1H), 7.15 (two d, 1H), 7.00-6.90 (m, 2H), 6.81 (m, 1H), 5.32 (m, 2H), 5.30-4.68 (m, 3H), 3.77 (s, 3H), 3.74 (m, 1H), 2.92-2.58 (m, 2H), 2.15 (m, 1H), 1.68 (m, 1H), 1.43 & 1.40 (two s, 9H), 0.95 (m, 3H)

Example 10)

5-Fluoro-3-2-[2-(3-methoxy-benzyl)-3-oxo-2,3-dihydro-pyridazin-4-yl]-butyr ylamino-4-oxo-pentanoic acid

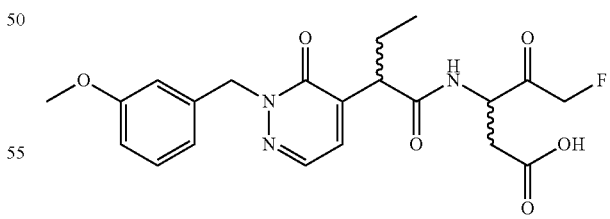

The compound of Preparation 10-2) (70 mg, 0.14 mmol) was reacted according to the same procedure as Example 2) to give the title compound (56 mg, 90%).

$^1$H-NMR (500 MHz, DMSO-d$_6$) δ 8.64 (br s, 1H), 7.88 (m, 1H), 7.30 (m, 1H), 7.19 (m, 1H), 6.80-6.77 (m, 3H), 5.41-4.80 (m, 2H), 5.28-5.14 (m, 2H), 4.57-4.49 (m, 1H), 3.67 (m, 3H), 3.65 (m, 1H), 2.71-2.32 (m, 2H), 1.74-1.63 (m, 2H), 0.82 (m, 3H)

Preparation 11-1)

2-(2-Naphthalen-1-ylmethyl-3-oxo-2,3-dihydro-pyridazin-4-yl)-butyric acid ethyl ester The compound of Preparation 6-6) (98 mg, 0.47 mmol) and 1-chloromethyl-naphthalene (107 mg, 1.3 eq) were reacted according to the same procedure as Preparation 2-1) to give the title compound (81 mg, 50%).

$^1$H-NMR (500 MHz, CDCl$_3$) δ 8.29 (d, 1H), 7.87-7.79 (m, 2H), 7.73 (d, 1H), 7.56-7.42 (m, 4H), 7.16 (d, 1H), 5.86-5.73 (ABq, 2H), 4.20-4.10 (m, 2H), 3.90 (m, 1H), 1.97 (m, 1H), 1.82 (m, 1H), 1.20 (t, 3H), 0.95 (t, 3H)

Preparation 11-2)

5-Fluoro-3-[2-(2-naphthalen-1-ylmethyl-3-oxo-2,3-dihydro-pyridazin-4-yl)-b utyrylamino]-4-oxo-pentanoic acid tert-butyl ester The compound of Preparation 11-1) (81 mg, 0.23 mmol) was reacted according to the same procedure as Preparation 3-5) to give the title compound (82 mg, 70%).

$^1$H-NMR (400 MHz, CDCl$_3$) δ 8.32 (two d, 1H), 7.91-7.81 (m, 3H), 7.65-7.46 (m, 5H), 7.19 (m, 1H), 5.89-5.80 (m, 2H), 5.28-4.75 (m, 3H), 3.83 (m, 1H), 2.96-2.65 (m, 2H), 2.18 (m, 1H), 1.75 (m, 1H), 1.47 & 1.42 (two s, 9H), 0.99 (m, 3H)

Example 11)

5-Fluoro-3-[2-(2-naphthalen-1-ylmethyl-3-oxo-2,3-dihydro-pyridazin-4-yl)-b utyrylamino]-4-oxo-pentanoic acid

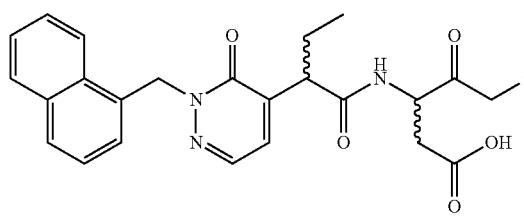

The compound of Preparation 11-2) (82 mg, 0.16 mmol) was reacted according to the same procedure as Example 2) to give the title compound (57 mg, 78%).

$^1$H-NMR (500 MHz, DMSO-d$_6$) δ 8.66 (br s, 1H), 8.20 (d, 1H), 7.93-7.84 (m, 3H), 7.52 (m, 2H), 7.42 (m, 1H), 7.31 (m, 1H), 7.26 (m, 1H), 5.70 (m, 2H), 5.43-4.80 (m, 2H), 4.55-4.48 (m, 1H), 3.72 (m, 1H), 2.70-2.33 (m, 2H), 1.75-1.65 (m, 2H), 0.84 (m, 3H)

Preparation 12-1)

2-(2-Naphthalen-2-ylmethyl-3-oxo-2,3-dihydro-pyridazin-4-yl)-butyric acid ethyl ester The compound of Preparation 6-6) (97 mg, 0.46 mmol) and 2-bromomethyl-naphthalene (132 mg, 1.3 eq) were reacted according to the same procedure as Preparation 2-1) to give the title compound (91 mg, 57%).

$^1$H-NMR (500 MHz, CDCl$_3$) δ 7.88 (s, 1H), 7.83-7.78 (m, 3H), 7.76 (d, 1H), 7.56 (d, 1H), 7.47-7.44 (m, 2H), 7.18 (d, 1H), 5.53-5.43 (ABq, 2H), 4.20-4.10 (m, 2H), 3.88 (m, 1H), 1.95 (m, 1H), 1.82 (m, 1H), 1.19 (t, 3H), 0.95 (t, 3H)

Preparation 12-2)

5-Fluoro-3-[2-(2-naphthalen-2-ylmethyl-3-oxo-2,3-dihydro-pyridazin-4-yl)-b utyrylamino]-4-oxo-pentanoic acid tert-butyl ester The compound of Preparation 12-1) (91 mg, 0.26 mmol) was reacted according to the same procedure as Preparation 3-5) to give the title compound (83 mg, 63%).

$^1$H-NMR (400 MHz, CDCl$_3$) δ 7.91 (d, 1H), 7.87-7.83 (m, 4H), 7.66-7.56 (m, 2H), 7.53-7.48 (m, 2H), 7.20 (t, 1H), 5.60-5.52 (m, 2H), 5.28-4.75 (m, 3H), 3.82 (m, 1H), 2.94-2.65 (m, 2H), 2.19 (m, 1H), 1.74 (m, 1H), 1.47 & 1.44 (two s, 9H), 1.00 (m, 3H)

Example 12)

5-Fluoro-3-[2-(2-naphthalen-2-ylmethyl-3-oxo-2,3-dihydro-pyridazin-4-yl)-b utyrylamino]-4-oxo-pentanoic acid

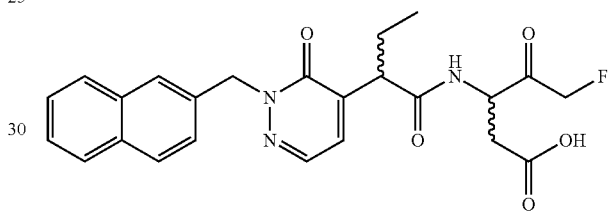

The compound of Preparation 12-2) (83 mg, 0.16 mmol) was reacted according to the same procedure as Example 2) to give the title compound (68 mg, 92%).

$^1$H-NMR (500 MHz, DMSO-d$_6$) δ 8.64 (br s, 1H), 7.90 (m, 1H), 7.85-7.83 (m, 3H), 7.76 (s, 1H), 7.46 (m, 2H), 7.42 (m, 1H), 7.31 (m, 1H), 5.44-5.34 (m, 2H), 5.31-4.73 (m, 2H), 4.57-4.49 (m, 1H), 3.69 (m, 1H), 2.63-2.32 (m, 2H), 1.75-1.63 (m, 2H), 0.82 (m, 3H)

Preparation 13-1)

(2-Methyl-oxazol-4-yl)-methanol

To LiAlH$_4$ (304 mg, 1.5 eq) was added anhydrous THF (20 mL). 2-Methyl-oxazole-4-carboxylic acid methyl ester (see *J. of Org. Chem.*, 2003, 68, p. 4215-4234) dissolved in THF (20 mL) was added thereto at −78° C., and stirred for 1 h at the same temperature. The reaction was stopped by water. The reaction mixture was passed through celite, and extracted with ethyl acetate (50 mL×3). The organic layer was washed with aqueous sodium chloride solution, distilled under reduced pressure, and separated by column chromatography (ethyl acetate) to give the title compound (308 mg, Yield: 51%) as a pale yellow solid.

$^1$H-NMR (400 MHz, CDCl$_3$) δ 7.48 (s, 1H), 4.56 (d, 2H), 2.45 (s, 3H), 2.18 (t, 1H)

Preparation 13-2)

4-Bromomethyl-2-methyl-oxazole

The compound of Preparation 13-1) (307 mg, 2.71 mmol) was dissolved in CH$_2$Cl$_2$ (20 mL), CBr$_4$ (1.17 g, 1.3 eq) and PPh₃ (1.07 g, 1.5 eq) were added thereto, and the mixture was stirred for 3 h. The reaction mixture was dried under reduced pressure and separated by column chromatography (25% ethyl acetate/hexane) to give the title compound (139 mg, Yield: 29%) as a colorless liquid.

¹H-NMR (400 MHz, CDCl₃) δ 7.58 (s, 1H), 4.39 (s, 2H), 2.50 (s, 3H)

Preparation 13-3)

2-[2-(2-Methyl-oxazol-4-ylmethyl)-3-oxo-2,3-dihydro-pyridazin-4-yl]-butyric acid ethyl ester The compound of Preparation 6-6) (160 mg, 0.761 mmol) and 4-bromomethyl-2-methyl-oxazole (139 mg, 1.3 eq) were reacted according to the same procedure as Preparation 2-1) to give the title compound (159 mg, 69%).

¹H-NMR (500 MHz, CDCl₃) δ 7.77 (d, 1H), 7.56 (s, 1H), 7.18 (d, 1H), 5.19 (ABq, 2H), 4.20-4.10 (m, 2H), 3.86 (t, 1H), 1.98-1.74 (two m, 2H), 1.22 (t, 3H), 0.94 (t, 3H)

Preparation 13-4)

5-Fluoro-3-2-[2-(2-methyl-oxazol-4-ylmethyl)-3-oxo-2,3-dihydro-pyridazin-4-yl]-butyrylamino-4-oxo-pentanoic acid tert-butyl ester The compound of Preparation 13-3) (155 mg, 0.508 mmol) was reacted according to the same procedure as Preparation 3-5) to give the title compound (150 mg, 64%).

¹H-NMR (500 MHz, CDCl₃) δ 7.80 (two d, 1H), 7.60-7.55 (m, 2H), 7.15 (m, 1H), 5.30-4.69 (m, 5H), 3.75 (m, 1H), 2.93-2.62 (m, 2H), 2.39 & 2.37 (two s, 3H), 2.12 (m, 1H), 1.66 (m, 1H), 1.41 & 1.38 (two s, 9H), 0.92 (m, 3H)

Example 13)

5-Fluoro-3-2-[2-(2-methyl-oxazol-4-ylmethyl)-3-oxo-2,3-dihydro-pyridazin-4-yl]-butyrylamino-4-oxo-pentanoic acid

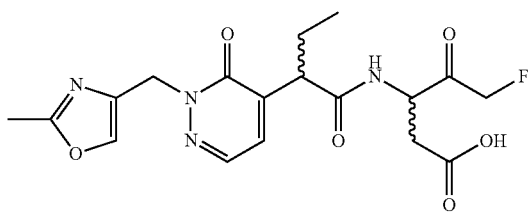

The compound of Preparation 13-4) (150 mg, 0.323 mmol) was reacted according to the same procedure as Example 2) to give the title compound (113 mg, 86%).

¹H-NMR (500 MHz, DMSO-d₆) δ 12.41 (br s, 1H), 8.70-8.63 (dd, 1H), 7.85 (m, 1H), 7.78 (m, 1H), 7.30 (m, 1H), 5.24-4.97 (m, 4H), 4.59-4.46 (m, 1H), 3.63 (m, 1H), 2.82-2.47 (m, 2H), 2.30 (s, 3H), 1.73-1.63 (m, 2H), 0.83 (m, 3H)

Preparation 14-1)

2-[2-(2-Methyl-thiazol-4-ylmethyl)-3-oxo-2,3-dihydro-pyridazin-4-yl]-butyric acid ethyl ester The compound of Preparation 6-6) (98 mg, 0.47 mmol) and 4-bromomethyl-2-methyl-thiazole (112 mg, 1.3 eq, Lancaster) were reacted according to the same procedure as Preparation 2-1) to give the title compound (101 mg, 67%).

¹H-NMR (500 MHz, CDCl₃) δ 7.79 (d, 1H), 7.20 (d, 1H), 7.05 (s, 1H), 5.45-5.37 (ABq, 2H), 4.20-4.10 (m, 2H), 3.88 (t, 1H), 2.68 (s, 3H), 1.96 & 1.81 (two m, 2H), 1.22 (t, 3H), 0.95 (t, 3H)

Preparation 14-2)

5-Fluoro-3-2-[2-(2-methyl-thiazol-4-ylmethyl)-3-oxo-2,3-dihydro-pyridazin-4-yl]-butyrylamino-4-oxo-pentanoic acid tert-butyl ester The compound of Preparation 14-1) (101 mg, 0.31 mmol) was reacted according to the same procedure as Preparation 3-5) to give the title compound (32 mg, 21%).

¹H-NMR (500 MHz, CDCl₃) δ 7.83 (two d, 1H), 7.58 (m, 2H), 7.20-7.03 (m, 2H), 5.51-4.69 (m, 5H), 3.75 (m, 1H), 2.93-2.62 (m, 2H), 2.64 (m, 3H), 2.12 (m, 1H), 1.66 (m, 1H), 1.41 & 1.38 (m, 9H), 0.94 (m, 3H)

Example 14)

5-Fluoro-3-2-[2-(2-methyl-thiazol-4-ylmethyl)-3-oxo-2,3-dihydro-pyridazin-4-yl]-butyrylamino-4-oxo-pentanoic acid

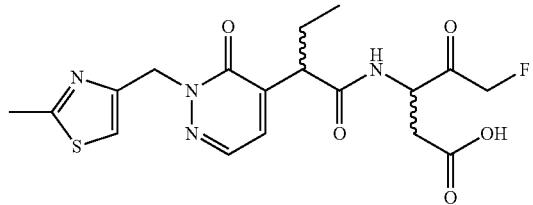 [SMILES: CCC(C(=O)NC(CC(=O)O)C(=O)CF)c1ccnn(Cc2coc(C)n2)c1=O]

The compound of Preparation 14-2) (32 mg, 0.066 mmol) was reacted according to the same procedure as Example 2) to give the title compound (16 mg, 58%).

¹H-NMR (500 MHz, CDCl₃) δ 7.82 (m, 1H), 7.80-7.76 (dd, 1H), 7.25 (s, 1H), 7.12 (m, 1H), 6.07-6.91 (m, 1H), 5.15-4.57 (m, 4H), 3.90 (m, 1H), 2.92-2.75 (m, 2H), 2.67 (s, 3H), 2.22-1.67 (m, 2H), 0.97 (m, 3H)

Preparation 15-1)

2-[2-(3,5-Dimethyl-isoxazol-4-ylmethyl)-3-oxo-2,3-dihydro-pyridazin-4-yl]-butyric acid ethyl ester The compound of Preparation 6-6) (96 mg, 0.46 mmol) and 4-chloromethyl-3,5-dimethyl-isoxazole (86 mg, 1.3 eq, Aldrich) were reacted according to the same procedure as Preparation 2-1) to give the title compound (119 mg, 82%).

¹H-NMR (500 MHz, CDCl₃) δ 7.71 (d, 1H), 7.18 (d, 1H), 5.10-5.02 (ABq, 2H), 4.20-4.10 (m, 2H), 3.85 (t, 1H), 2.46 (s, 3H), 2.32 (s, 3H), 1.98-1.74 (two m, 2H), 1.22 (t, 3H), 0.95 (t, 3H)

Preparation 15-2)

3-2-[2-(3,5-Dimethyl-isoxazol-4-ylmethyl)-3-oxo-2,3-dihydro-pyridazin-4-yl]-butyrylamino-5-fluoro-4-oxo-pentanoic acid tert-butyl ester The compound of Preparation 15-1) (119 mg, 0.37 mmol) was reacted according to the same procedure as Preparation 3-5) to give the title compound (47 mg, 40%).

¹H-NMR (400 MHz, CDCl₃) δ 7.79 (two d, 1H), 7.48 (m, 1H), 7.21 (d, 2H), 5.30-4.79 (m, 5H), 3.77 (m, 1H), 2.97-2.69 (m, 2H), 2.54 (two s, 3H), 2.36 (s, 1H), 2.16 (m, 1H), 1.72 (m, 1H), 1.47 & 1.42 (two s, 9H), 0.99 (m, 3H)

Example 15)

3-2-[2-(3,5-Dimethyl-isoxazol-4-ylmethyl)-3-oxo-2,3-dihydro-pyridazin-4-yl]-butyrylamino-5-fluoro-4-oxo-pentanoic acid

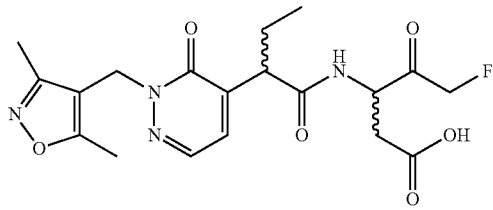 [SMILES: CCC(C(=O)NC(CC(=O)O)C(=O)CF)c1ccnn(Cc2c(C)noc2C)c1=O]

The compound of Preparation 15-2) (47 mg, 0.098 mmol) was reacted according to the same procedure as Example 2) to give the title compound (27 mg, 66%).

¹H-NMR (500 MHz, DMSO-d₆) δ 8.64 (br s, 1H), 7.86 (dd, 1H), 7.28 (m, 1H), 5.32-4.91 (m, 2H), 5.08-4.96 (m, 2H), 4.56-4.47 (m, 1H), 3.66 (m, 1H), 2.63-2.32 (m, 2H), 2.37 (s, 3H), 2.16 (s, 3H), 1.72-1.63 (m, 2H), 0.82 (m, 3H)

Preparation 16-1)

2-(2-Cyclohexylmethyl-3-oxo-2,3-dihydro-pyridazin-4-yl)-butyric acid ethyl ester The compound of Preparation 6-6) (101 mg, 0.48 mmol) and bromomethyl-cyclohexane (111 mg, 1.3 eq, Aldrich) were reacted according to the same procedure as Preparation 2-1) to give the title compound (82 mg, 56%).

¹H-NMR (500 MHz, CDCl₃) δ 7.71 (d, 1H), 7.16 (d, 1H), 4.20-4.10 (m, 2H), 4.14-3.94 (m, 2H), 3.86 (t, 1H), 1.98-1.74 (two m, 2H), 1.72-1.60 (broad m, 5H), 1.23 (t, 3H), 1.20-1.16 (broad m, 3H), 1.05-1.00 (m, 2H), 0.96 (t, 3H)

Preparation 16-2)

3-[2-(2-Cyclohexylmethyl-3-oxo-2,3-dihydro-pyridazin-4-yl)-butyrylamino]-5-fluoro-4-oxo-pentanoic acid tert-butyl ester The compound of Preparation 16-1) (80 mg, 0.26 mmol) was reacted according to the same procedure as Preparation 3-5) to give the title compound (106 mg, 88%).

¹H-NMR (500 MHz, CDCl₃) δ 7.77 (m, 1H), 7.64 (m, 1H), 7.14 (m, 1H), 5.29-4.72 (m, 3H), 4.10-3.98 (m, 2H), 3.76 (m, 1H), 2.94-2.62 (m, 2H), 2.15 (m, 1H), 1.94 (m, 1H), 1.72-1.60 (broad m, 5H), 1.43 & 1.41 (two s, 9H), 1.23-1.00 (m, 5H), 0.96 (m, 3H)

Example 16)

3-[2-(2-Cyclohexylmethyl-3-oxo-2,3-dihydro-pyridazin-4-yl)-butyrylamino]-5-fluoro-4-oxo-pentanoic acid

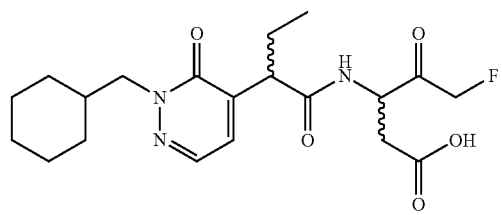 [SMILES: CCC(C(=O)NC(CC(=O)O)C(=O)CF)c1ccnn(CC2CCCCC2)c1=O]

The compound of Preparation 16-2) (106 mg, 0.23 mmol) was reacted according to the same procedure as Example 2) to give the title compound (71 mg, 76%).

¹H-NMR (500 MHz, DMSO-d₆) δ 8.65 (br s, 1H), 7.83 (m, 1H), 7.26 (m, 1H), 5.35-4.88 (m, 2H), 4.57-4.48 (m, 1H), 3.97-3.82 (m, 2H), 3.63 (m, 1H), 2.66-2.47 (m, 2H), 1.79 (m, 1H), 1.73 (m, 1H), 1.61 (m, 3H), 1.55 (m, 1H), 1.49 (m, 2H), 1.10 (m, 3H), 0.95 (m, 2H), 0.82 (m, 3H)

Preparation 17-1)

1-Bromomethyl-isoquinoline

To 1-methylisoquinoline (0.99 g, 6.91 mmol), NBS (1.35 g, 1.1 eq) and AIBN (10 mg, catalytic amount) was added CCl₄ (15 mL), which was then refluxed for 2 h. The suspended particles were removed by filtration, and washed with CCl₄. The organic layers were combined, concentrated under reduced pressure, and separated by column chromatography (30%, ethyl acetate/hexane) to give the title compound (270 mg, Yield: 18%) as a violet solid.

¹H-NMR (500 MHz, CDCl₃) δ 8.48 (d, 1H), 8.25 (d, 1H), 7.87 (d, 1H), 7.75-7.67 (two t, 2H), 7.65 (d, 1H)

Preparation 17-2)

2-(2-Isoquinolin-1-ylmethyl-3-oxo-2,3-dihydro-pyridazin-4-yl)-butyric acid ethyl ester The compound of Preparation 6-6) (110 mg, 0.52 mmol) and 1-bromomethyl-isoquinoline (151 mg, 1.3 eq) obtained in Preparation 17-1) were reacted according to the same procedure as Preparation 2-1) to give the title compound (135 mg, 73%).

¹H-NMR (500 MHz, CDCl₃) δ 8.42 (d, 1H), 8.26 (d, 1H), 7.82 (d, 1H), 7.77 (d, 1H), 7.60 (t, 1H), 7.57 (d, 1H), 7.22 (d, 1H), 6.06-5.91 (ABq, 2H), 4.21-4.10 (m, 2H), 3.91 (t, 1H), 2.01-1.78 (two m, 2H), 1.21 (t, 3H), 0.96 (t, 3H)

Preparation 17-3)

5-Fluoro-3-[2-(2-isoquinolin-1-ylmethyl-3-oxo-2,3-dihydro-pyridazin-4-yl)-butyrylamino]-4-oxo-pentanoic acid tert-butyl ester The compound of Preparation 17-2) (130 mg, 0.37 mmol) was reacted according to the same procedure as Preparation 3-5) to give the title compound (150 mg, 79%).

¹H-NMR (500 MHz, CDCl₃) δ 8.39 (d, 1H), 8.27 (d, 1H), 7.88-7.80 (m, 2H), 7.73-7.56 (m, 3H), 7.22 (m, 1H), 6.12-5.95 (m, 2H), 5.23-4.68 (m, 3H), 3.80 (m, 1H), 2.92-2.58 (m, 2H), 2.19 (m, 1H), 1.75 (m, 1H), 1.34 (m, 9H), 0.96 (m, 3H)

Example 17)

5-Fluoro-3-[2-(2-isoquinolin-1-ylmethyl-3-oxo-2,3-dihydro-pyridazin-4-yl)-bu tyrylamino]-4-oxo-pentanoic acid

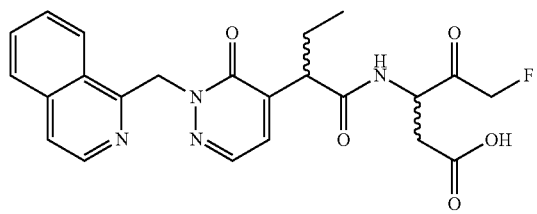 [SMILES: CCC(C(=O)NC(CC(=O)O)C(=O)CF)c1ccnn(Cc2nccc3ccccc23)c1=O]

The compound of Preparation 17-3) (150 mg, 0.29 mmol) was reacted according to the same procedure as Example 2) to give the title compound (123 mg, 92%).

¹H-NMR (500 MHz, DMSO-d₆) δ 12.42 (br s, 1H), 8.74-8.64 (dd, 1H), 8.28 (m, 2H), 7.98 (d, 1H), 7.87 (m, 1H), 7.79 (m, 1H), 7.72-7.65 (m, 2H), 7.37 (m, 1H), 5.92 (m, 2H), 5.22-5.00 (m, 2H), 4.60-4.48 (m, 1H), 3.67 (m, 1H), 2.74-2.54 (m, 2H), 1.77-1.65 (m, 2H), 0.84 (m, 3H)

Preparation 18-1)

2-[2-(2-Chloro-benzyl)-3-oxo-2,3-dihydro-pyridazin-4-yl]-butyric acid ethyl ester The compound of Preparation 6-6) (100 mg, 0.476 mmol) and 1-bromomethyl-2-chlorobenzene (127 mg, 1.3 eq, Aldrich) were reacted according to the same procedure as Preparation 2-1) to give the title compound (92 mg, 58%).

¹H-NMR (500 MHz, CDCl₃) δ 7.77 (d, 1H), 7.37 (d, 1H), 7.23-7.16 (m, 3H), 7.07 (d, 1H), 5.51-5.43 (ABq, 2H), 4.21-4.10 (m, 2H), 3.90 (t, 1H), 2.02-1.79 (two m, 2H), 1.22 (t, 3H), 0.96 (t, 3H)

Preparation 18-2)

3-{2-[2-(2-Chloro-benzyl)-3-oxo-2,3-dihydro-pyridazin-4-yl]-butyrylamino}-5-fluoro-4-oxo-pentanoic acid tert-butyl ester The compound of Preparation 18-1) (92 mg, 0.275 mmol) was reacted according to the same procedure as Preparation 3-5) to give the title compound (113 mg, 83%).

¹H-NMR (500 MHz, CDCl₃) δ 7.82 (two d, 1H), 7.54 (m, 1H), 7.38 (m, 1H), 7.24-7.18 (m, 3H), 7.09-7.02 (m, 1H), 5.54-5.44 (m, 2H), 5.21-4.71 (m, 3H), 3.79 (m, 1H), 2.90-2.56 (m, 2H), 2.16 (m, 1H), 1.73 (m, 1H), 1.41 & 1.38 (two d, 9H), 0.96 (m, 3H)

Example 18)

3-{2-[2-(2-Chloro-benzyl)-3-oxo-2,3-dihydro-pyridazin-4-yl]-butyrylamino}-5-fluoro-4-oxo-pentanoic acid

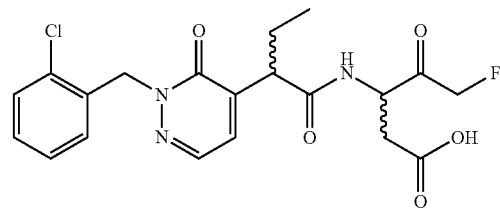 [SMILES: CCC(C(=O)NC(CC(=O)O)C(=O)CF)c1ccnn(Cc2ccccc2Cl)c1=O]

The compound of Preparation 18-2) (103 mg, 0.29 mmol) was reacted according to the same procedure as Example 2) to give the title compound (74 mg, 81%).

¹H-NMR (500 MHz, DMSO-d₆) δ 8.63 (br, 1H), 7.91 (m, 1H), 7.45-7.25 (m, 4H), 7.00 (m, 1H), 5.32 (m, 2H), 5.30-4.60 (br, 2H), 4.57 & 4.50 (two br m, 1H), 3.69 (m, 1H), 2.70-2.50 (br, 2H), 1.77-1.65 (m, 2H), 0.84 (m, 3H)

Preparation 19-1)

2-[2-(3-Chloro-benzyl)-3-oxo-2,3-dihydro-pyridazin-4-yl]-butyric acid ethyl ester The compound of Preparation 6-6) (98 mg, 0.466 mmol) and 1-bromomethyl-3-chlorobenzene (127 mg, 1.3 eq, Aldrich) were reacted according to the same procedure as Preparation 2-1) to give the title compound (115 mg, 74%).

¹H-NMR (500 MHz, CDCl₃) δ 7.74 (d, 1H), 7.38 (s, 1H), 7.28-7.21 (m, 3H), 7.18 (d, 1H), 5.32-5.22 (ABq, 2H), 4.21-4.10 (m, 2H), 3.84 (t, 1H), 1.99-1.75 (two m, 2H), 1.20 (t, 3H), 0.94 (t, 3H)

Preparation 19-2)

3-{2-[2-(3-Chloro-benzyl)-3-oxo-2,3-dihydro-pyridazin-4-yl]-butyrylamino}-5-fluoro-4-oxo-pentanoic acid tert-butyl ester The compound of Preparation 19-1) (115 mg, 0.343 mmol) was reacted according to the same procedure as Preparation 3-5) to give the title compound (130 mg, 77%).

¹H-NMR (500 MHz, CDCl₃) δ 7.80 (m, 1H), 7.54 (d, 1H), 7.38 (d, 1H), 7.30-7.23 (m, 3H), 7.18 (m, 1H), 5.31-5.25 (m, 2H), 5.21-4.71 (m, 3H), 3.76 (m, 1H), 2.91-2.62 (m, 2H), 2.14 (m, 1H), 1.69 (m, 1H), 1.43 & 1.39 (two d, 9H), 0.96 (m, 3H)

Example 19)

3-{2-[2-(3-Chloro-benzyl)-3-oxo-2,3-dihydro-pyridazin-4-yl]-butyrylamino}-5-fluoro-4-oxo-pentanoic acid

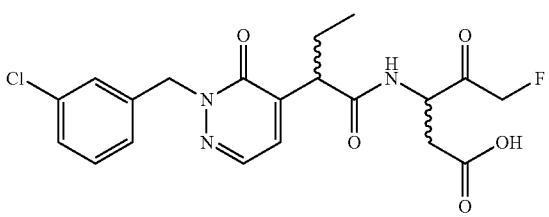

The compound of Preparation 19-2) (120 mg, 0.243 mmol) was reacted according to the same procedure as Example 2) to give the title compound (87 mg, 82%).

¹H-NMR (500 MHz, DMSO-d₆) δ 8.62 (br, 1H), 7.89 (m, 1H), 7.32-7.30 (m, 4H), 7.20 (m, 1H), 5.28-5.18 (m, 2H), 5.20-4.60 (br, 2H), 4.58 & 4.50 (two br m, 1H), 3.66 (m, 1H), 2.70-2.50 (br, 2H), 1.77-1.58 (m, 2H), 0.84 (m, 3H)

Preparation 20-1)

2-[2-(3-Bromo-benzyl)-3-oxo-2,3-dihydro-pyridazin-4-yl]-butyric acid ethyl ester The compound of Preparation 6-6) (100 mg, 0.48 mmol) and 1-bromo-3-bromomethylbenzene (154 mg, 1.3 eq, Aldrich) were reacted according to the same procedure as Preparation 2-1) to give the title compound (102 mg, 54%).

¹H NMR (500 MHz, CDCl₃); δ 0.95 (t, 3H), 0.96 (t, 3H), 1.78-1.95 (m, 2H), 3.85 (t, 1H), 4.15 (m, 2H), 5.27 (q, 2H), 7.17-7.45 (m, 5H), 7.54 (s, 1H), 7.75 (d, 1H)

Preparation 20-2)

3-{2-[2-(3-Bromo-benzyl)-3-oxo-2,3-dihydro-pyridazin-4-yl]-butyrylamino}-5-fluoro-4-oxo-pentanoic acid tert-butyl ester The compound of Preparation 20-1) (100 mg, 0.254 mmol) was reacted according to the same procedure as Preparation 3-5) to give the title compound (120 mg, 88%).

¹H NMR (500 MHz, CDCl₃); δ 0.96 (m, 3H), 1.41 (d, 9H), 1.69 (m, 1H), 2.13 (m, 1H), 2.60-2.91 (m, 2H), 3.76 (m, 1H), 4.77 (m, 1H), 5.01 (m, 2H), 5.29 (m, 2H), 7.18 (m, 2H), 7.30-7.45 (m, 2H), 7.52 (m, 2H), 7.80 (m, 1H)

Example 20)

3-{2-[2-(3-Bromo-benzyl)-3-oxo-2,3-dihydro-pyridazin-4-yl]-butyrylamino}-5-fluoro-4-oxo-pentanoic acid

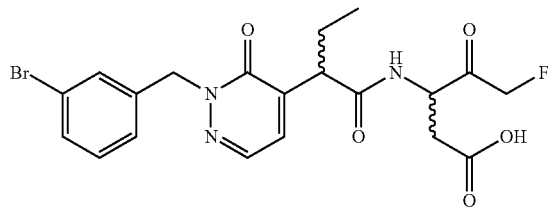 [SMILES: CCC(C(=O)NC(CC(=O)O)C(=O)CF)c1ccnn(Cc2cccc(Cl)c2)c1=O]

The compound of Preparation 20-2) (80 mg, 0.15 mmol) was reacted according to the same procedure as Example 2) to give the title compound (59 mg, 81%).

¹H NMR (500 MHz, CDCl₃); δ 0.96 (m, 3H), 1.68 (m, 1H), 2.06 (m, 1H), 2.50-3.16 (m, 2H), 3.84 (m, 1H), 4.77 (m, 3H), 5.29 (m, 2H), 7.19-7.52 (m, 6H), 7.91 (m, 1H)

Preparation 21-1)

2-[3-Oxo-2-(2-trifluoromethyl-benzyl)-2,3-dihydro-pyridazin-4-yl]-butyric acid ethyl ester The compound of Preparation 6-6) (104 mg, 0.50 mmol), DIAD(diisopropyl azodicarboxylate, 151 mg, 1.5 eq), (2-trifluoromethyl-phenyl)-methanol (131 mg, 1.5 eq) and triphenylphosphine (261 mg, 2.0 eq) were dissolved in THF (6 mL), and stirred for 2 h at room temperature. The mixture was concentrated under reduced pressure and separated by column chromatography (30% EA/Hexane) to give the title compound (125 mg, 68%).

¹H-NMR (500 MHz, CDCl₃) δ 7.79 (d, 1H), 7.67 (d, 1H), 7.44 (t, 1H), 7.36 (t, 1H), 7.26 (d, 1H), 6.97 (d, 1H), 5.62-5.54 (ABq, 2H), 4.21-4.12 (m, 2H), 3.90 (t, 1H), 2.03-1.81 (two m, 2H), 1.22 (t, 3H), 0.97 (t, 3H)

Preparation 21-2)

5-Fluoro-4-oxo-3-{2-[3-oxo-2-(2-trifluoromethyl-benzyl)-2,3-dihydro-pyridazi n-4-yl]-butyrylamino}-pentanoic acid tert-butyl ester The compound of Preparation 21-1) (125 mg, 0.34 mmol) was reacted according to the same procedure as Preparation 3-5) to give the title compound (48 mg, 27%).

¹H-NMR (500 MHz, CDCl₃) δ 7.83 (two d, 1H), 7.68 (m, 1H), 7.51-7.44 (m, 2H), 7.36 (d, 1H), 7.23 (d, 1H), 7.00-6.92 (two d, 1H), 5.69-5.51 (m, 2H), 5.21-4.73 (m, 3H), 3.78 (m, 1H), 2.90-2.58 (m, 2H), 2.16 (m, 1H), 1.75 (m, 1H), 1.37 (m, 9H), 0.96 (m, 3H)

Example 21)

5-Fluoro-4-oxo-3-{2-[3-oxo-2-(2-trifluoromethyl-benzyl)-2,3-dihydro-pyridazi n-4-yl]-butyrylamino}-pentanoic acid

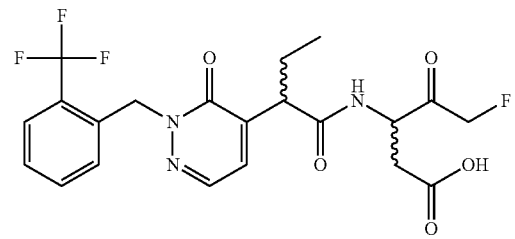 [SMILES: CCC(C(=O)NC(CC(=O)O)C(=O)CF)c1ccnn(Cc2ccccc2C(F)(F)F)c1=O]

The compound of Preparation 21-2) (48 mg, 0.092 mmol) was reacted according to the same procedure as Example 2) to give the title compound (37 mg, 86%).

¹H-NMR (500 MHz, CDCl₃) δ 7.92 (dd, 1H), 7.70 (d, 1H), 7.60 (bs, 1H), 7.45 (t, 1H), 7.39 (t, 1H), 7.35 (m, 1H), 6.95 (d, 1H), 5.64-5.51 (m, 2H), 4.77-4.35 (m, 3H), 3.84 (m, 1H), 3.06-2.90 (m, 1H), 2.68-2.58 (m, 1H), 2.12 (m, 1H), 1.74 (m, 1H), 0.97 (t, 3H)

Preparation 22-1)

2-[3-Oxo-2-(3-trifluoromethyl-benzyl)-2,3-dihydro-pyridazin-4-yl]-butyric acid ethyl ester The compound of Preparation 6-6) (100 mg, 0.48 mmol), DIAD(diisopropyl azodicarboxylate, 192 mg, 2.0 eq), (3-trifluoromethyl-phenyl)-methanol (168 mg, 2.0 eq) and triphenylphosphine (312 mg, 2.5 eq) were dissolved in THF (6 mL), and stirred for 2 h at room temperature. The mixture was concentrated under reduced pressure and separated by column chromatography (30% EA/Hexane) to give the title compound (158 mg, 90%).

¹H-NMR (500 MHz, CDCl₃) δ 7.76 (d, 1H), 7.65 (s, 1H), 7.60 (d, 1H), 7.53 (d, 1H), 7.43 (t, 1H), 7.20 (d, 1H), 5.40-5.30 (ABq, 2H), 4.20-4.08 (m, 2H), 3.85 (t, 1H), 2.01-1.76 (two m, 2H), 1.19 (t, 3H), 0.94 (t, 3H)

Preparation 22-2)

5-Fluoro-4-oxo-3-{2-[3-oxo-2-(3-trifluoromethyl-benzyl)-2,3-dihydro-pyridazi n-4-yl]-butyrylamino}-pentanoic acid tert-butyl ester The compound of Preparation 22-1) (157 mg, 0.43 mmol) was reacted according to the same procedure as Preparation 3-5) to give the title compound (93 mg, 41%).
¹H-NMR (500 MHz, CDCl₃) δ 7.80 (two d, 1H), 7.65 (two s, 1H), 7.60 (m, 1H), 7.52 (m, 2H), 7.44 (m, 1H), 7.18 (two d, 1H), 5.42-5.33 (m, 2H), 5.18-4.71 (m, 3H), 3.74 (m, 1H), 2.90-2.60 (m, 2H), 2.12 (m, 1H), 1.68 (m, 1H), 1.42 & 1.38 (two s, 9H), 0.94 (m, 3H)

Example 22)

5-Fluoro-4-oxo-3-{2-[3-oxo-2-(3-trifluoromethyl-benzyl)-2,3-dihydro-pyridazi n-4-yl]-butyrylamino}-pentanoic acid

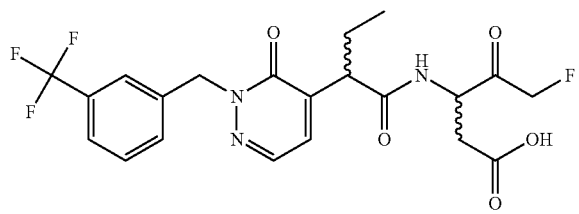 [SMILES: CCC(C(=O)NC(CC(=O)O)C(=O)CF)c1ccnn(Cc2cccc(C(F)(F)F)c2)c1=O]

The compound of Preparation 22-2) (93 mg, 0.18 mmol) was reacted according to the same procedure as Example 2) to give the title compound (75 mg, 90%).
¹H-NMR (500 MHz, CDCl₃) δ 7.90 (dd, 1H), 7.65 (s, 1H), 7.57 (m, 2H), 7.45 (t, 1H), 7.32 (m, 1H), 5.37 (m, 2H), 4.86-4.35 (m, 3H), 3.84-3.96 (m, 1H), 3.13-2.92 (m, 1H), 2.70-2.59 (m, 1H), 2.08 (m, 1H), 1.69 (m, 1H), 0.96 (t, 3H)

Preparation 23-1)

(3S)-3-{[(benzyloxy)carbonyl]amino}-5-(tert-butoxy)-2-hydroxy-5-oxopentyl 2,6-dichlorobenzoate To N-benzyloxycarbonyl-β-t-butyl-aspartic acid (5.03 g, 15.6 mmol) and NMM (1.90 mL, 17.1 mmol) was added anhydrous tetrahydrofuran (60 mL) under nitrogen atmosphere, which was maintained at −15° C. Isobutylchloroformate (2.12 mL, 16.3 mmol) was added, and the mixture was stirred for about 20 min. To the reaction mixture maintained at 0° C. was added diazomethane-ether solution (synthesized from 2.0 eq of 1-methyl-3-nitro-1-nitroso-guanidine, 60 mL), which was then stirred for 30 min at 0° C. to give the diazoketone derivative. 30% HBr/AcOH (6.42 mL, 2.0 eq) was added thereto at 0° C., and stirred for 30 min. The reaction mixture was extracted with ethyl acetate, washed with water, twice with saturated aqueous sodium hydrogen carbonate solution, and aqueous sodium chloride solution, dried (anhydrous Na₂SO₄), and concentrated under reduced pressure to give the bromomethylketone derivative (6.4 g).

The bromomethylketone derivative (4.36 g) and 2,6-dichlorobenzoic acid (2.28 g, 1.1 eq) were dissolved in dimethylformamide (18 mL), KF (1.58 g, 2.5 eq) was added thereto, and the mixture was stirred for 2 h at room temperature. The residue obtained by concentration under reduced pressure was extracted with ethyl acetate, washed with water, twice with saturated aqueous sodium hydrogen carbonate solution, and aqueous sodium chloride solution, dried (anhydrous Na₂SO₄), and concentrated under reduced pressure to give the 2,6-dichlorobenzoxymethylketone derivative. This compound was dissolved in methanol (20 mL), and reacted by adding NaBH₄ (412 mg)-methanol solution (40 mL). The reaction mixture was slowly warmed to room temperature for 2 h. The reaction was stopped by acetic acid. The reaction mixture was distilled under reduced pressure to remove methanol, extracted with ethyl acetate (50 mL×2), washed with water and aqueous sodium chloride solution, dried (anhydrous Na₂SO₄), concentrated under reduced pressure, and separated by column chromatography (ethyl acetate-hexane, 1:5) to give 4.80 g (86%) of the title compound.
¹H-NMR (400 MHz, CDCl₃) δ 7.3-7.2 (m, 8H), 5.9 (m, 1H), 5.2 (m, 4H), 4.7 (m, 1H), 2.9 (m, 1H), 2.7 (m, 1H), 1.4 (s, 9H)

Preparation 23-2)

(3S)-3-amino-5-(tert-butoxy)-2-hydroxy-5-oxopentyl 2,6-dichlorobenzoate

The compound of Preparation 23-1) (4.80 g, 9.37 mmol) was dissolved in EtOH, and subjected to debenzyloxycarbonylation (Pd/C) under hydrogen balloon for 40 min to give 3.47 g (98%) of the title compound.
¹H-NMR (400 MHz, DMSO-d) δ 8.2 (br, 2H), 7.6-7.5 (m, 3H), 6.1 (m, 1H), 4.4-3.9 (m, 3H), 3.0-2.6 (m, 2H), 1.4 (s, 9H)

Preparation 23-3)

2,6-Dichloro-benzoic acid (S)-4-tert-butoxycarbonyl-3-{2-[2-(2-tert-butyl-benzyl)-3-oxo-2,3-dihydro-pyridazin-4-yl]-butyrylamino}-2-oxo-butyl ester The compound of Preparation 6-8) was hydrolyzed according to the same procedure as Preparation 2-3) to give the carboxylic acid derivative. A mixture of this carboxylic acid derivative (100 mg, 0.304 mmol), the compound of Preparation 23-2) (151 mg, 1.2 eq) and HATU (337 mg, 1.3 eq) was cooled to 0° C., triethylamine (0.17 mL, 4.0 eq) was added thereto in DMF solvent (4 mL), and the mixture was reacted for 1 h. The solvent was distilled under reduced pressure. The residue was extracted with ethyl acetate (30 mL×2), washed with water, aqueous sodium hydrogen carbonate solution and aqueous sodium chloride solution, dried (anhydrous Na₂SO₄), and concentrated under reduced pressure to give 2,6-dichloro-benzoic acid (S)-4-tert-butoxycarbonyl-3-{2-[2-(2-tert-butyl-benzyl)-3-oxo-2,3-dihydro-pyridazin-4-yl]-butyrylamino}-2-hydroxy-butyl ester. To this compound and Dess-Martin reagent (260 mg, 2.0 eq) was added anhydrous dichloromethane (4 mL), which was then stirred for 0.5 h at room temperature. The reaction was stopped by isopropyl alcohol (1 mL). The solid was removed by celite filtration under reduced pressure, and extracted with ethyl acetate (20 mL×2). The extract was washed with water, saturated aqueous sodium hydrogen carbonate solution and aqueous sodium chloride solution, dried (anhydrous Na₂SO₄), and concentrated under reduced pressure. The residue was separated by column chromatography (20-25% ethyl acetate-hexane) to give 163 mg (78%) of the title compound.

$^1$H-NMR (500 MHz, CDCl$_3$) δ 7.84 (m, 1H), 7.62 (m, 1H), 7.43 (t, 1H), 7.34-7.25 (m, 4H), 7.16 (m, 1H), 7.06 (t, 1H), 6.83-6.74 (two d, 1H), 5.86-5.52 (m, 2H), 5.22-4.81 (m, 3H), 3.86 (m, 1H), 2.89-2.62 (m, 2H), 2.02 (m, 1H), 1.75 (m, 1H), 1.49 & 1.48 (two s, 9H), 1.41 & 1.37 (two s, 9H), 0.99 (m, 3H)

Example 23-1) and 23-2)

2,6-Dichloro-benzoic acid (S)-3-{(R)-2-[2-(2-tert-butyl-benzyl)-3-oxo-2,3-dihydro-pyridazin-4-yl]-butyrylamino}-4-carboxy-2-oxo-butyl ester and 2,6-Dichloro-benzoic acid (S)-3-{(S)-2-[2-(2-tert-butyl-benzyl)-3-oxo-2,3-dihydro-pyridazin-4-yl]-butyrylamino}-4-carboxy-2-oxo-butyl ester

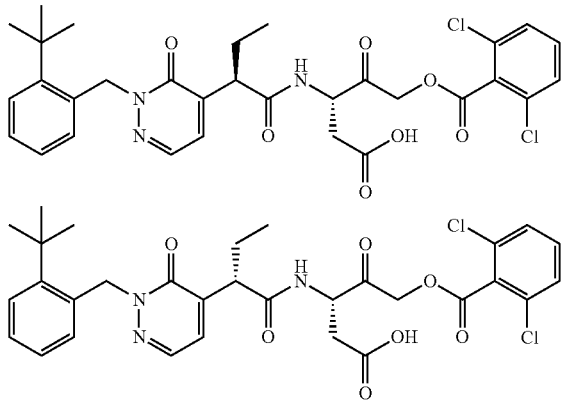

The compound of Preparation 23-3) (159 mg, 0.29 mmol) was reacted according to the same procedure as Example 2) to give the title compound as a mixture of two diastereomers, which was then separated by Prep-TLC (70% EtOAc/Hexane) to give 62 mg (42%) and 50 mg (34%) of each diastereomer. The compound with lower polarity on TLC was assigned as Example 23-1 and the compound with higher polarity as Example 23-2, but their specific diastereomer forms were not identified.

Compound with lower polarity: $^1$H-NMR (500 MHz, DMSO-d$_6$) δ 8.78 (br, 1H), 7.93 (m, 1H), 7.56-7.52 (m, 3H), 7.40 (m, 1H), 7.34 (t, 1H), 7.11 (m, 1H), 7.05 (m, 1H), 6.67 (d, 1H), 5.58-5.42 (ABq, 2H), 5.30-4.60 (br m, 3H), 4.58 & 4.50 (two br m, 1H), 3.72 (m, 1H), 2.70-2.50 (br, 2H), 1.82-1.63 (m, 2H), 1.40 (m, 9H), 0.85 (m, 3H) (Example 23-1)

Compound with higher polarity: $^1$H-NMR (500 MHz, DMSO-d$_6$) δ 8.74 (br, 1H), 7.93 (m, 1H), 7.57-7.51 (m, 3H), 7.40 (d, 1H), 7.34 (d, 1H), 7.11 (m, 1H), 7.02 (m, 1H), 6.67 (d, 1H), 5.56-5.43 (ABq, 2H), 5.26-5.00 (br m, 2H), 4.72 (m, 1H), 3.70 (m, 1H), 2.76-2.50 (br, 2H), 1.82-1.63 (m, 2H), 1.38 (s, 9H), 0.85 (t, 3H) (Example 23-2)

Preparation 24-1) tert-butyl (3S)-3-amino-4-hydroxy-5-(2,3,5,6-tetrafluorophenoxy)pentanoate N-benzyloxycarbonyl-β-t-butyl-aspartic acid (17.9 g, 55.5 mmol) and 2,3,5,6-tetrafluorophenol were reacted according to the same procedure as Preparation 23-1) and 23-2) to give 13.2 g (68%) of the title compound.

$^1$H-NMR (400 MHz, DMSO-d$_6$) δ 8.2 (br, 2H), 7.6-7.5 (m, 1H), 5.9 (m, 1H), 4.3-4.1 (m, 3H), 3.6 (m, 1H), 2.7 (m, 1H), 1.4 (s, 9H)

Preparation 24-2)

(S)-3-{(R)-2-[2-(2-tert-Butyl-benzyl)-3-oxo-2,3-dihydro-pyridazin-4-yl]-butyr ylamino}-4-oxo-5-(2,3,5,6-tetrafluoro-phenoxy)-pentanoic acid tert-butyl ester and; (S)-3-{(S)-2-[2-(2-tert-Butyl-benzyl)-3-oxo-2,3-dihydro-pyridazin-4-yl]-butyr ylamino}-4-oxo-5-(2,3,5,6-tetrafluoro-phenoxy)-pentanoic acid tert-butyl ester

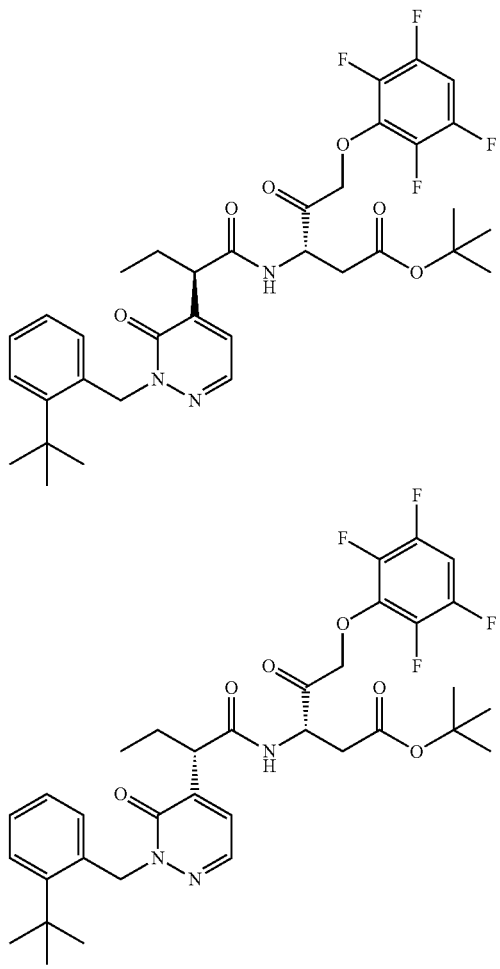

The compound of Preparation 6-8) (104 mg, 0.29 mol) was hydrolyzed according to the same procedure as Preparation 2-3) to give the carboxylic acid derivative. A mixture of this carboxylic acid derivative (95 mg, 0.29 mmol), the compound of Preparation 24-1) (113 mg, 1.2 eq) and HATU (143 mg, 1.3 eq) was cooled to 0° C., triethylamine (0.16 mL, 4.0 eq) was added thereto in DMF solvent (5 mL), and the mixture was reacted for 2 h. The solvent was distilled under reduced pressure. The residue was extracted with ethyl acetate (30 mL×2), washed with water, aqueous sodium hydrogen carbonate solution and aqueous sodium chloride solution, dried (anhydrous Na$_2$SO$_4$), concentrated under reduced pressure, and preliminarily purified by Prep-TLC (500% EA/Hexane) to give 172 mg (89%) of (S)-3-{2-[2-(2-tert-butyl-benzyl)-3-oxo-2,3-dihydro-pyridazin-4-yl]-butyrylamino}-4-hydroxy-5-(2,3,5,6-tetrafluoro-phenoxy)-pentanoic acid tert-butyl ester. To this compound and Dess-Martin reagent (220 mg, 2.0 eq) was added anhydrous dichloromethane (4 mL), which was then stirred for 1 h at room temperature. The reaction was stopped by isopropyl alcohol (1 mL). The solid was removed by celite filtration under reduced pressure, and extracted with ethyl acetate (20 mL×2). The extract was washed with water, saturated aqueous sodium hydrogen carbonate solution and aqueous sodium chloride solution, dried (anhydrous Na$_2$SO$_4$), and concentrated under reduced pressure. The residue was purified by Prep-TLC (30% EA/Hexane) to give 74 mg (38%) of the title diastereomer with lower polarity and 67 mg (35%) with higher polarity.

Diastereomer with Lower Polarity:
$^1$H-NMR (500 MHz, CDCl$_3$) δ 7.83 (d, 1H), 7.59 (d, 1H), 7.42 (d, 1H), 7.22 (d, 1H), 7.17 (t, 1H), 7.06 (t, 1H), 6.76 (m, 1H), 6.73 (d, 1H), 5.65 (Abq, 2H), 5.19-5.02 (Abq, 2H), 4.75 (m, 1H), 3.81 (dd, 1H), 2.76 (dd, 1H), 2.59 (dd, 1H), 2.19 (m, 1H), 1.73 (m, 1H), 1.48 (s, 9H), 1.34 (s, 9H), 0.98 (t, 3H)

Diastereomer with Higher Polarity:
$^1$H-NMR (500 MHz, CDCl$_3$) δ 7.83 (d, 1H), 7.61 (d, 1H), 7.39 (d, 1H), 7.23 (d, 1H), 7.14 (t, 1H), 7.05 (t, 1H), 6.78 (d, 1H), 6.72 (m, 1H), 5.74-5.58 (Abq, 2H), 5.07-4.83 (Abq, 2H), 4.82 (m, 1H), 3.80 (dd, 1H), 2.89 (dd, 1H), 2.68 (dd, 1H), 2.16 (m, 1H), 1.75 (m, 1H), 1.48 (s, 9H), 1.39 (s, 9H), 0.96 (t, 3H)

Example 24-1) and 24-2)

(S)-3-{(R)-2-[2-(2-tert-Butyl-benzyl)-3-oxo-2,3-dihydro-pyridazin-4-yl]-butyr ylamino}-4-oxo-5-(2,3,5,6-tetrafluoro-phenoxy)-pentanoic acid and (S)-3-{(S)-2-[2-(2-tert-Butyl-benzyl)-3-oxo-2,3-dihydro-pyridazin-4-yl]-butyr ylamino}-4-oxo-5-(2,3,5,6-tetrafluoro-phenoxy)-pentanoic acid

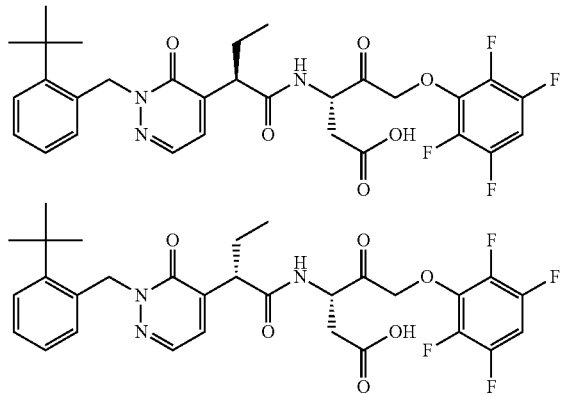

The compound with lower polarity prepared in Preparation 24-2) (74 mg, 0.11 mmol) was reacted according to the same procedure as Example 2) to give one of the title compounds (58 mg, 87%) which was assigned as Example 24-1).

$^1$H-NMR (500 MHz, CDCl$_3$) δ 7.91 (d, 1H), 7.43 (d, 1H), 7.39 (bs, 1H), 7.18 (t, 1H), 7.05 (t, 1H), 6.75 (m, 1H), 6.70 (d, 1H), 5.65 (s, 2H), 5.40-4.50 (m, 3H), 3.95 (m, 1H), 3.01 (m, 1H), 2.55 (m, 1H), 2.13 (m, 1H), 1.73 (m, 1H), 1.47 (s, 9H), 0.97 (t, 3H) (Example 24-1)

The compound with higher polarity prepared in Preparation 24-2) (67 mg, 0.10 mmol) was reacted according to the same procedure as Example 2) to give the other of the title compounds (60 mg, 98%) which was assigned as Example 24-2).

$^1$H-NMR (500 MHz, CDCl$_3$) δ 7.91 (d, 1H), 7.42 (d, 1H), 7.31 (bs, 1H), 7.16 (t, 1H), 7.03 (t, 1H), 6.75 (m, 1H), 6.70 (d, 1H), 5.65 (s, 2H), 4.89-4.03 (m, 3H), 3.76 (m, 1H), 2.99 (m, 1H), 2.70 (m, 1H), 2.12 (m, 1H), 1.75 (m, 1H), 1.48 (s, 9H), 0.97 (t, 3H) (Example 24-2)

Preparation 25-1)

(S)-3-{2-[2-(3-tert-Butyl-benzyl)-3-oxo-2,3-dihydro-pyridazin-4-yl]-butyryla mino}-4-oxo-5-(2,3,5,6-tetrafluoro-phenoxy)-pentanoic acid tert-butyl ester The compound of Preparation 7-2) (135 mg, 0.38 mmol) was reacted according to the same procedure as Preparation 24-2) to give the title compound (198 mg, 79%).

$^1$H-NMR (500 MHz, CDCl$_3$) δ 7.79 (two d, 1H), 7.63 (m, 1H), 7.42 (two s, 1H), 7.32-7.14 (m, 4H), 6.73 (m, 1H), 5.43-5.21 (m, 2H), 5.20-4.71 (m, 3H), 3.77 (m, 1H), 2.93-2.59 (m, 2H), 2.15 (m, 1H), 1.69 (m, 1H), 1.43 & 1.40 (two s, 9H), 1.29 (s, 9H), 0.95 (m, 3H)

Example 25-1) and 25-2)

(S)-3-{(R)-2-[2-(3-tert-Butyl-benzyl)-3-oxo-2,3-dihydro-pyridazin-4-yl]-butyr ylamino}-4-oxo-5-(2,3,5,6-tetrafluoro-phenoxy)-pentanoic acid and (S)-3-{(S)-2-[2-(3-tert-Butyl-benzyl)-3-oxo-2,3-dihydro-pyridazin-4-yl]-butyr ylamino}-4-oxo-5-(2,3,5,6-tetrafluoro-phenoxy)-pentanoic acid

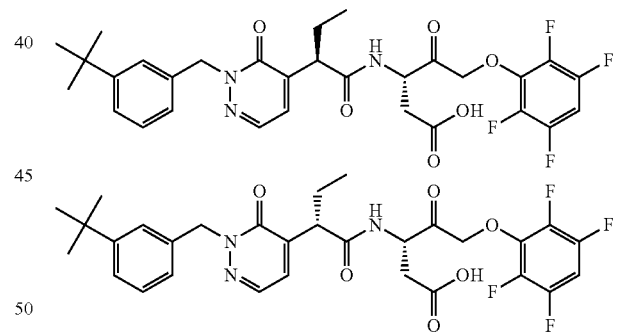

The compound of Preparation 25-1) (75 mg, 0.11 mmol) was reacted according to the same procedure as Example 2) to give the title compound as a mixture of two diastereomers, which was then separated by Prep-TLC (70% EtOAc/Hexane) to give 31 mg (44%) of a diastereomer with lower polarity (Example 25-1) and 33 mg (48%) of a diastereomer with higher polarity (Example 25-2).

Diastereomer with lower polarity: $^1$H-NMR (500 MHz, DMSO-d$_6$) δ 8.70 (m, 1H), 7.87 (d, 1H), 7.50 (m, 1H), 7.30 (s, 1H), 7.24 (d, 2H), 7.18 (m, 1H), 6.97 (m, 1H), 5.24-5.03 (m, 4H), 4.64-4.52 (m, 1H), 3.68 (m, 1H), 2.68-2.58 (m, 2H), 1.73 (m, 1H), 1.63 (m, 1H), 1.19 (s, 9H), 0.82 (m, 3H) (Example 25-1)

Diastereomer with higher polarity: $^1$H-NMR (500 MHz, DMSO-d$_6$) δ 8.66 (m, 1H), 7.87 (d, 1H), 7.50 (m, 1H), 7.30 (s, 1H), 7.25 (two d, 2H), 7.16 (m, 1H), 6.96 (m, 1H), 5.23-4.90 (m, 4H), 4.63-4.54 (m, 1H), 3.68 (m, 1H), 2.68-2.50 (m, 2H), 1.73 (m, 1H), 1.63 (m, 1H), 1.19 (s, 9H), 0.82 (m, 3H) (Example 25-2)

Preparation 26-1)

(S)-2-Amino-succinic acid 4-tert-butyl ester 1-methyl ester hydrochloride

To Cbz-Asp(O-tert-Bu)-OH.H$_2$O (5.00 g, 14.6 mmol) and K$_2$CO$_3$ (4.05 g, 2.0 eq) were added DMF (100 mL) and MeI (2.74 mL, 3 eq), which was then stirred for 2-3 h at room temperature. The solvent was distilled under reduced pressure. The residue was extracted with ethyl acetate (100 mL×2), washed with water, aqueous sodium hydrogen carbonate solution and aqueous sodium chloride solution, dried (anhydrous Na$_2$SO$_4$), and concentrated under reduced pressure. The residue was purified by column chromatography (30% ethyl acetate/hexane) to give (S)-2-benzyloxycarbonylamino-succinic acid 4-tert-butyl ester 1-methyl ester in a stoichiometric yield. This compound was dissolved in MeOH (100 mL), c-HCl (1.1 mL, 1.0 eq) was added, and subjected to debenzyloxycarbonylation (Pd/C) for 40 min under hydrogen balloon, whereby giving 3.28 g (96%) of the title compound.

Preparation 26-2)

(S)-2-{2-[2-(2-tert-Butyl-benzyl)-3-oxo-2,3-dihydro-pyridazin-4-yl]-butyryla mino}-succinic acid 4-tert-butyl ester 1-methyl ester The compound of Preparation 6-8) was hydrolyzed according to the same procedure as Preparation 2-3) to give the carboxylic acid derivative. A mixture of this carboxylic acid derivative (938 mg, 2.86 mmol), the compound of Preparation 26-1) (753 mg, 1.1 eq) and HATU (1.41 g, 1.3 eq) was cooled to 0° C., triethylamine (2.00 mL, 5.0 eq) was added thereto in DMF solvent (18 mL), and the mixture was reacted for 1 h at room temperature. The solvent was distilled under reduced pressure. The residue was extracted with ethyl acetate (50 mL×2), washed with water, aqueous sodium hydrogen carbonate solution and aqueous sodium chloride solution, dried (anhydrous Na$_2$SO$_4$), and concentrated under reduced pressure. The residue was purified by column chromatography (50% ethyl acetate-hexane) to give 1.24 g (84%) of the title compound.

$^1$H-NMR (400 MHz, CDCl$_3$) δ 7.84 (dd, 1H), 7.48 (d, 1H), 7.41-7.32 (dd, 1H), 7.30 (d, 1H), 7.23 (m, 1H), 7.14 (m, 1H), 6.92-6.83 (dd, 1H), 5.76-5.65 (m, 2H), 4.82 (m, 1H), 3.91 (m, 1H), 3.76, 3.68 (two s, 3H), 2.92-2.63 (m, 2H), 2.19 (m, 1H), 1.76 (m, 1H), 1.55 (s, 9H), 1.46, 1.42 (two s, 9H), 1.02 (m, 3H).

Preparation 26-3)

(S)-5-Bromo-3-{2-[2-(2-tert-butyl-benzyl)-3-oxo-2, 3-dihydro-pyridazin-4-yl]-butyrylamino}-4-oxo-pentanoic acid tert-butyl ester The compound of Preparation 26-2) (1.24 g, 2.41 mmol) was hydrolyzed according to the same procedure as Preparation 2-3) to give the carboxylic acid derivative (1.15 g, 95%). To this carboxylic acid derivative (1.15 g, 2.30 mmol) and NMM (0.28 mL, 2.53 mmol) was added anhydrous tetrahydrofuran (20 mL) under nitrogen atmosphere, which was maintained at 0° C. Isobutylchloroformate (0.31 mL, 2.42 mmol) was added, and the mixture was stirred for about 30 min. To the reaction mixture maintained at 0° C. was added diazomethane-ether solution (synthesized from 4.0 eq of 1-methyl-3-nitro-1-nitroso-guanidine, 40 mL), which was then stirred for 4 h at 0° C. to give the diazoketone derivative. 30% HBr/AcOH (1.02 mL, 2.0 eq) was added thereto at 0° C., and stirred for 30 min. The reaction mixture was extracted with ethyl acetate, washed with water, twice with saturated aqueous sodium hydrogen carbonate solution, and aqueous sodium chloride solution, dried (anhydrous Na$_2$SO$_4$), and concentrated under reduced pressure to give the bromomethylketone derivative (1.30 g, 98%). This compound was used in the next reaction without further purification.

$^1$H-NMR (500 MHz, CDCl$_3$) δ 7.84 (dd, 1H), 7.63-7.58 (dd, 1H), 7.43 (d, 1H), 7.25-7.17 (m, 2H), 7.09 (m, 1H), 6.83-6.75 (dd, 1H), 5.74-5.62 (m, 2H), 4.91, 4.82 (two m, 1H), 4.12-3.93 (m, 2H), 3.79 (m, 1H), 2.91-2.60 (m, 2H), 2.17 (m, 1H), 1.74 (m, 1H), 1.49 (s, 9H), 1.40, 1.36 (two s, 9H), 0.97 (m, 3H).

Preparation 26-4)

(S)-3-{2-[2-(2-tert-Butyl-benzyl)-3-oxo-2,3-dihydro-pyridazin-4-yl]-butyryla mino}-4-oxo-5-(2,3,6-trifluoro-phenoxy)-pentanoic acid tert-butyl ester The compound of Preparation 26-3) (100 mg, 0.17 mmol) and 2,3,6-trifluoro-phenol (31 mg, 1.2 eq) were dissolved in dimethylformamide (2 mL), KF (25 mg, 2.5 eq) was added thereto, and the mixture was stirred for 4 h at room temperature. The residue obtained by concentration under reduced pressure was extracted with ethyl acetate, washed with water, twice with saturated aqueous sodium hydrogen carbonate solution, and aqueous sodium chloride solution, dried (anhydrous Na$_2$SO$_4$), and concentrated under reduced pressure. The residue was purified by Prep-TLC (70% ethyl acetate/hexane) to give 77 mg (69%) of the title compound.

$^1$H-NMR (500 MHz, CDCl$_3$) δ 7.82 (m, 1H), 7.56 (m, 1H), 7.42 (t, 1H), 7.23 (t, 1H), 7.16 (m, 1H), 7.06 (m, 1H), 6.82-6.73 (m, 3H), 5.76-5.55 (m, 2H), 5.10-4.78 (m, 3H), 3.82 (m, 1H), 2.94-2.60 (m, 2H), 2.16 (m, 1H), 1.73 (m, 1H), 1.46 (s, 9H), 1.39, 1.34 (two s, 9H), 0.95 (m, 3H).

Example 26-1) and 26-2)

(S)-3-{(R)-2-[2-(2-tert-Butyl-benzyl)-3-oxo-2,3-dihydro-pyridazin-4-yl]-butyr ylamino}-4-oxo-5-(2,3,6-trifluoro-phenoxy)-pentanoic acid and (S)-3-{(S)-2-[2-(2-tert-Butyl-benzyl)-3-oxo-2,3-dihydro-pyridazin-4-yl]-butyr ylamino}-4-oxo-5-(2,3,6-trifluoro-phenoxy)-pentanoic acid

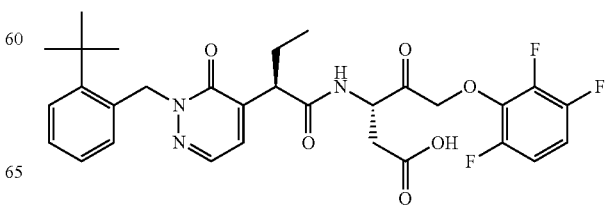

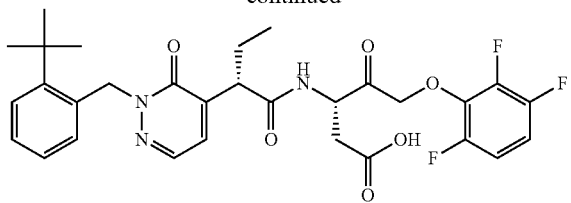

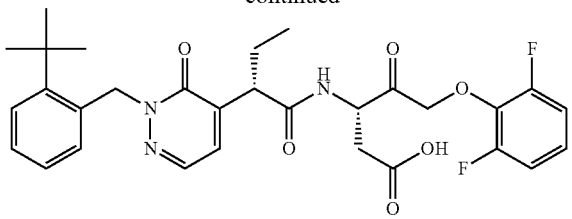

The compound of Preparation 26-4) (77 mg, 0.12 mmol) was reacted according to the same procedure as Example 2) to give the title compound as a mixture of two diastereomers, which was then separated by Prep-TLC (50% ethyl acetate/hexane) to give 24 mg (34%) of a diastereomer with lower polarity (Example 26-1) and 17 mg (24%) of a diastereomer with higher polarity (Example 26-2).

Diastereomer with lower polarity: $^1$H-NMR (500 MHz, CDCl$_3$) δ 7.89 (d, 1H), 7.43 (d, 1H), 7.30 (m, 1H), 7.18 (t, 1H), 7.05 (t, 1H), 6.83 (m, 2H), 6.71 (d, 1H), 5.67-5.63 (m, 2H), 4.82-4.10 (m, 3H), 3.84 (m, 1H), 2.86 (m, 1H), 2.52 (m, 1H), 2.16 (m, 1H), 1.73 (m, 1H), 1.48 (s, 9H), 0.95 (t, 3H).

Diastereomer with higher polarity: $^1$H-NMR (500 MHz, CDCl$_3$) δ 7.90 (d, 1H), 7.41 (d, 1H), 7.32 (m, 1H), 7.15 (t, 1H), 7.02 (t, 1H), 6.79 (m, 2H), 6.70 (d, 1H), 5.63 (m, 2H), 4.89-4.05 (m, 3H), 3.90 (m, 1H), 3.05 (m, 1H), 2.69 (m, 1H), 2.12 (m, 1H), 1.73 (m, 1H), 1.47 (s, 9H), 0.96 (m, 3H).

Preparation 27)

(S)-3-{2-[2-(2-tert-Butyl-benzyl)-3-oxo-2,3-dihydro-pyridazin-4-yl]-butyryla mino}-5-(2,6-difluoro-phenoxy)-4-oxo-pentanoic acid tert-butyl ester The compound of Preparation 26-3) (100 mg, 0.17 mmol) and 2,6-difluoro-phenol (27 mg, 1.2 eq) were dissolved in dimethylformamide (2 mL), KF (25 mg, 2.5 eq) was added thereto, and the mixture was stirred for 4 h at room temperature. The residue obtained by concentration under reduced pressure was extracted with ethyl acetate, washed with water, twice with saturated aqueous sodium hydrogen carbonate solution, and aqueous sodium chloride solution, dried (anhydrous Na$_2$SO$_4$), and concentrated under reduced pressure. The residue was purified by Prep-TLC (70% ethyl acetate/hexane) to give 77 mg (71%) of the title compound.

$^1$H-NMR (500 MHz, CDCl$_3$) δ 7.79 (m, 1H), 7.54 (m, 1H), 7.41 (m, 1H), 7.23 (m, 1H), 7.16 (m, 1H), 7.05 (m, 1H), 6.92-6.72 (m, 4H), 5.76-5.52 (m, 2H), 5.02-4.73 (m, 3H), 3.84 (m, 1H), 2.97-2.62 (m, 2H), 2.15 (m, 1H), 1.71 (m, 1H), 1.48 (s, 9H), 1.40, 1.34 (two s, 9H), 0.96 (m, 3H).

Example 27-1) and 27-2)

(S)-3-{(R)-2-[2-(2-tert-Butyl-benzyl)-3-oxo-2,3-dihydro-pyridazin-4-yl]-butyr ylamino}-5-(2,6-difluoro-phenoxy)-4-oxo-pentanoic acid (S)-3-{(S)-2-[2-(2-tert-Butyl-benzyl)-3-oxo-2,3-dihydro-pyridazin-4-yl]-butyr ylamino}-5-(2,6-difluoro-phenoxy)-4-oxo-pentanoic acid

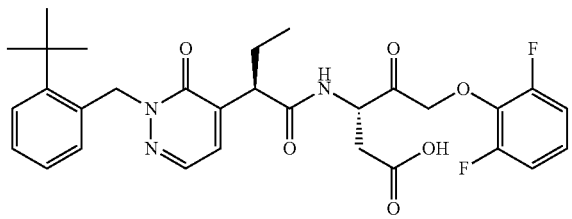

The compound of Preparation 27) (75 mg, 0.11 mmol) was reacted according to the same procedure as Example 2) to give the title compound as a mixture of two diastereomers, which was then separated by Prep-TLC (50% EtOAc/Hexane) to give 25 mg (36%) of a diastereomer with lower polarity (Example 27-1) and 24 mg (35%) of a diastereomer with higher polarity (Example 27-2).

Diastereomer with lower polarity: $^1$H-NMR (500 MHz, CDCl$_3$) δ 7.88 (d, 1H), 7.43 (d, 1H), 7.28 (m, 1H), 7.18 (t, 1H), 7.05 (t, 1H), 6.97 (m, 1H), 6.87 (t, 2H), 6.71 (d, 1H), 5.67-5.63 (m, 2H), 4.77-4.10 (m, 3H), 3.82 (m, 1H), 2.83 (m, 1H), 2.51 (m, 1H), 2.14 (m, 1H), 1.71 (m, 1H), 1.48 (s, 9H), 0.95 (t, 3H)

Diastereomer with higher polarity: $^1$H-NMR (500 MHz, CDCl$_3$) δ 7.87 (d, 1H), 7.41 (d, 1H), 7.29 (m, 1H), 7.16 (t, 1H), 7.03 (t, 1H), 6.93 (m, 1H), 6.83 (t, 2H), 6.72 (d, 1H), 5.67-5.62 (m, 2H), 4.88-4.10 (m, 3H), 3.87 (m, 1H), 3.04 (m, 1H), 2.67 (m, 1H), 2.11 (m, 1H), 1.72 (m, 1H), 1.46 (s, 9H), 0.96 (t, 3H).

Preparation 28)

(S)-3-{2-[2-(2-tert-Butyl-benzyl)-3-oxo-2,3-dihydro-pyridazin-4-yl]-butyryla mino}-5-(diphenyl-phosphinoyloxy)-4-oxo-pentanoic acid tert-butyl ester The compound of Preparation 26-3) (100 mg, 0.17 mmol) and diphenylphosphinic acid (45 mg, 1.2 eq) were dissolved in dimethylformamide (2 mL), KF (25 mg, 2.5 eq) was added thereto, and the mixture was stirred for 4 h at room temperature. The residue obtained by concentration under reduced pressure was extracted with ethyl acetate, washed with water, twice with saturated aqueous sodium hydrogen carbonate solution, and aqueous sodium chloride solution, dried (anhydrous Na$_2$SO$_4$), and concentrated under reduced pressure. The residue was purified by Prep-TLC (50% ethyl acetate/hexane) to give 80 mg (65%) of the title compound.

$^1$H-NMR (500 MHz, CDCl$_3$) δ 7.87-7.76 (m, 5H), 7.56-7.41 (m, 8H), 7.18-7.14 (m, 2H), 7.07 (m, 1H), 6.83-6.72 (dd, 1H), 5.77-5.56 (m, 2H), 4.94-4.62 (m, 3H), 3.77 (m, 1H), 2.79-2.54 (m, 2H), 2.09 (m, 1H), 1.68 (m, 1H), 1.48 (s, 9H), 1.36 & 1.31 (two s, 9H), 0.89 (m, 3H).

Example 28)

(S)-3-{2-[2-(2-tert-Butyl-benzyl)-3-oxo-2,3-dihydro-pyridazin-4-yl]-butyryla mino}-5-(diphenyl-phosphinoyloxy)-4-oxo-pentanoic acid

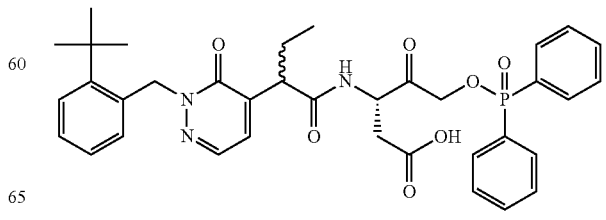

The compound of Preparation 28) (80 mg, 0.11 mmol) was reacted according to the same procedure as Example 2), concentrated under reduced pressure, and separated by Prep-TLC (10% MeOH/CH$_2$Cl$_2$) to give 68 mg (91%) of the title compound as a mixture of two diastereomers.

$^1$H-NMR (500 MHz, CDCl$_3$) δ 7.80-7.71 (m, 5H), 7.52-7.40 (m, 7H), 7.20 (m, 1H), 7.15 (m, 1H), 7.04 (m, 1H), 6.75 (m, 1H), 5.72-5.49 (m, 2H), 4.76-4.10 (m, 3H), 3.84 (m, 1H), 2.93-2.54 (m, 2H), 1.98 (m, 1H), 1.65 (m, 1H), 1.46 (s, 9H), 0.87-0.79 (m, 3H).

Experiment 1

Determination of the Caspase Inhibitory Effect

Caspase-1 and caspase-8 known as cysteine proteases in the form of α$_2$β$_2$ were expressed, purified, and activated by modifying a method known in Thornberry, N. A. et al, *Nature*, 1992, 356, 768. Thornberry, N. A. *Methods in Enzymology*, 1994, 244, 615. Walker, N. P. C. et al. *Cell*, 1994, 78, 343, and caspase-9 was also purified by a similar method, and the inhibitory activity against them was tested. Briefly describing, p10 and p20 subunits (Thornberry, N. A. et al, *Nature*, 1992, 356, 768) were expressed in *E. coli* and purified by nickel column and anionic exchange chromatography to give caspase-1, caspase-8 and caspase-9. The fluorescent substrates AcYVAD-AFC for thus obtained caspase-1, AcDEVD-AFC for caspase-8, and AcLEHD-AFC for caspase-9, were used for determining specific activity of the synthesized inhibitors. The enzyme reaction was carried out at 25° C. with various concentrations of the inhibitors in a buffer solution containing 50 mM HEPES(pH 7.50), 10% (w/v) sucrose, 0.1% (w/v) CHAPS, 100 mM NaCl, 1 mM EDTA, and 10 mM DTT in the presence of 50 µM AcYVAD-AFC for 10 nM caspase-1, 50 µM AcDEVD-AFC for 2.1 nM caspase-8, and 150 µM AcLEHD-AFC for 200 nM caspase-9. The inhibitory constants K$_i$ and K$_{obs}$ of the inhibitors were determined by measuring the reaction velocity with the time lapse using a fluorescent spectrometer and by obtaining the initial rate constant. K$_i$ was calculated from the Lineweaver Burk Plot, and K$_{obs}$ from the following Equation 1.

$$K_{obs} = -\ln(1 - A_t/A_{oo})/t \quad \text{[Equation 1]}$$

in which

A$_t$ means cleavage rate (%) at time t, and

A$_{oo}$ means the maximum cleavage rate (%).

Spectra MAX GeminiXS Fluorescent Spectrometer of Molecular Device Co. was used at the excitation wavelength of 405 nm and the emission wavelength of 505 nm.

The in vivo inhibitory activity of the inhibitors was determined by subjecting Jurkat cell (ATCC TIB-152) to apoptosis using Fas antibody (Upstate Biotech 05-201) and by detecting the color change according to the WST-1 method known in Francoeur A. M. and Assalian A. (1996) Biochemica 3, 19-25 to observe the amount of alive Jurkat cells when the cells were treated by the inhibitor. Spectra MAX 340 Spectrometer of Molecular Device Co. was used at the absorbance wavelength of 440 nm.

TABLE 1

| Example No. | Caspase-8 K$_{obs}$/[I] (M$^{-1}$min$^{-1}$) | Jurkat Cell IC$_{50}$ (µM) |
|---|---|---|
| 1 | 5.8 E4 | 8.0 |
| 2 | 4.4 E5 | 1.48 |
| 3 | 1.3 E6 | 0.46 |
| 4 | 4.1 E5 | 0.39 |
| 5 | 2.3 E5 | 2.07 |
| 6 | 3.8 E6 | 0.042 |
| 7 | 1.4 E6 | 0.035 |
| 8 | 1.2 E6 | 0.82 |
| 9 | 3.0 E6 | 0.88 |
| 10 | 1.2 E6 | 0.55 |
| 11 | 3.4 E6 | 0.17 |
| 12 | 9.3 E5 | 0.29 |
| 13 | 6.9 E5 | 3.76 |
| 14 | 8.4 E5 | 0.73 |
| 15 | 7.2 E5 | 0.80 |
| 16 | 7.4 E5 | 0.09 |
| 17 | 1.5 E6 | 0.13 |
| 18 | 4.4 E6 | 0.042 |
| 19 | 1.7 E6 | 0.035 |
| 20 | 1.1 E6 | 0.043 |
| 21 | 4.0 E6 | 0.043 |
| 22 | 8.6 E5 | 0.216 |
| 23-1 | 1.2 E6 | 0.14 |
| 23-2 | 5.6 E4 | 2.48 |
| 24-1 | 3.8 E6 | 0.012 |
| 24-2 | 1.1 E5 | 4.15 |
| 25-1 | 1.6 E6 | 0.031 |
| 25-2 | 5.4 E4 | 1.94 |
| 26-1 | 1.7 E6 | 0.045 |
| 26-2 | 4.7 E5 | — |
| 27-1 | 7.0 E5 | 0.090 |
| 27-2 | 1.9 E5 | — |
| 28 | 3.4 E6 | 0.365 |

Experiment 2

Therapeutic Effect for Liver Injury Induced by Antibody Against Fas in Mouse

Step 1) Preparation of Blood Sample

Male Balb/c mice (6 weeks, Charles River Laboratory, Osaka, Japan) were kept under the conditions of 22□, 55% of relative humidity, and light-darkness cycle of 12 hours. Food and water were supplied ad libitum. In pyrogen-free phosphate buffer was dissolved the antibody against Fas (Jo2; BD pharmingen, San Diego, Calif.), which was then injected to each mouce in the amount of 0.15 mg/kg through the vein of tail. Immediately after the injection of the Fas antibody, vehicle (a mixture of PEG400: ethanol=2:1 was 20-fold diluted with phosphate buffer) wherein the test compound is dissolved or the vehicle alone was orally administered to the mice. After 6 hours from the drug administration, blood samples were obtained from their hearts.

Step 2: Determination of the Activity of Plasma Aminotransferase

The plasma ALT activity was determined for the blood samples obtained in Step 1 using ALT assay kit (Asan Pharm. Co., Seoul, Korea) according to the manufacturer's instruction. The results appeared that the injection of the Fas antibody sharply increases the ALT activity in plasma, and the test compounds inhibit the increased enzyme activity in a dose-dependent manner. Based on these results, ED$_{50}$ values of the test compounds were calculated using Prism software of GraphPad Co. to give 0.001-10 mg/kg.

INDUSTRIAL APPLICABILITY

As the above results of Experiments show, the compound of formula (1) of the present invention has an excellent inhibitory activity against caspase, and particularly exhibits a therapeutic effect in the animal model of liver injury induced by the Fas antibody. Therefore, the compound of formula (1) can be advantageously used for the treatment of various diseases and symptoms mediated by caspase.

The invention claimed is:

1. A compound of formula (1):

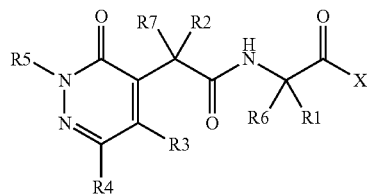

[Formula 1]

in which

I) $R^1$ represents H, $C_1$-$C_5$-alkyl, $C_3$-$C_{10}$-cycloalkyl, aryl, or a side chain of a natural amino acid selected from the group consisting of —$CH_3$, —$(CH_2)_3$—NH—$C(NH_2)$=NH, —$CH_2$—CO—$NH_2$, —$CH_2$—COOH, —$CH_2$—SH, —$(CH_2)_2$—CO—$NH_2$, —$(CH_2)_2$—COOH,

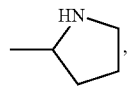

—CH($CH_3$)—$CH_2$—$CH_3$, —$CH_2$—CH—$(CH_3)_2$, —$(CH_2)_4$—$NH_2$, —$(CH_2)_2$—S—$CH_3$, —$CH_2$-phenyl

—$CH_2$—OH, —CH(OH)—$CH_3$,

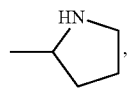

—$CH_2$-phenyl-OH, and —CH—$(CH_3)_2$

II) $R^2$ represents H, $C_1$-$C_5$-alkyl, $C_3$-$C_{10}$-cycloalkyl, aryl, or a side chain of a natural amino acid selected from the group consisting of $CH_3$, —$(CH_2)_3$—NH—$C(NH_2)$=NH, —$CH_2$—CO—$NH_2$, —$CH_2$—COOH, —$CH_2$—SH, —$(CH_2)_2$—CO—$NH_2$, —$(CH_2)_2$—COOH,

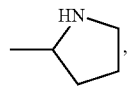

—CH($CH_3$)—$CH_2$—$CH_3$, —$CH_2$—CH—$(CH_3)_2$, —$(CH_2)_4$—$NH_2$, —$(CH_2)_2$—S—$CH_3$, —$CH_2$-phenyl,

—$CH_2$—OH, —CH(OH)—$CH_3$,

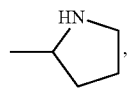

—$CH_2$-phenyl-OH, and —CH—$(CH_3)_2$

III) $R^3$ represents H, $C_1$-$C_5$-alkyl, hydroxy, $C_1$-$C_5$-alkoxy, or halogen, IV) $R^4$ represents H, $C_1$-$C_5$-alkyl, $C_3$-$C_{10}$-cycloalkyl, or aryl, V) $R^5$ represents H, $C_1$-$C_5$-alkyl, $C_3$-$C_{10}$-cycloalkyl, or aryl, VI) $R^6$ and $R^7$ independently of one another each represent H, $C_1$-$C_5$-alkyl, $C_3$-$C_{10}$-cycloalkyl, or aryl, VII) X represents —$CH_2OR^9$ ($R^9$ is $C_1$-$C_5$-alkyl, $C_3$-$C_{10}$-cycloalkyl, or aryl), —$CH_2OC(=O)R^{10}$ ($R^{10}$ is $C_1$-$C_5$-alkyl, $C_3$-$C_{10}$-cycloalkyl, or aryl), —$CH_2$—OP(=O)$R_2^{11}$ ($R^{11}$ is $C_1$-$C_5$-alkyl, $C_3$-$C_{10}$-cycloalkyl, or aryl), or —$CH_2$—W (W is halogen), or pharmaceutically acceptable salt thereof.

2. The compound of claim 1 wherein $R^5$ represents $C_1$-$C_5$-alkyl substituted by $C_3$-$C_{10}$-cycloalkyl which is unsubstituted or substituted by one or more substituents selected from the group consisting of $C_1$-$C_5$-alkyl, hydroxy, $C_1$-$C_5$-alkoxy and halogen, or by aryl which is unsubstituted or substituted by one or more substituents selected from the group consisting of $C_1$-$C_5$-alkyl, hydroxy, $C_1$-$C_5$-alkoxy and halogen; or represents aryl which is unsubstituted or substituted by one or more substituents selected from the group consisting of $C_1$-$C_5$-alkyl, hydroxy, $C_1$-$C_5$-alkoxy and halogen, or pharmaceutically acceptable salt thereof.

3. The compound of claim 1 wherein

I) $R^1$ represents a side chain of a natural amino acid selected from the group consisting of $CH_3$, —$(CH_2)_3$—NH—$C(NH_2)$=NH, —$CH_2$—CO—$NH_2$, —$CH_2$—COOH, —$CH_2$—SH, —$(CH_2)_2$—CO—$NH_2$, —$(CH_2)_2$—COOH,

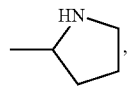

—CH($CH_3$)—$CH_2$—$CH_3$, —$CH_2$—CH—$(CH_3)_2$, —$(CH_2)_4$—$NH_2$, —$(CH_2)_2$—S—$CH_3$, —$CH_2$-phenyl,

—$CH_2$—OH, —CH(OH)—$CH_3$,

—CH$_2$-phenyl-OH, and —CH—(CH$_3$)$_2$

II) R$^2$ represents C$_1$-C$_5$-alkyl,

III) R$^3$ represents H, C$_1$-C$_5$-alkyl, C$_1$-C$_5$-alkoxy, or halogen,

IV) R$^4$ represents H,

V) R$^5$ represents C$_1$-C$_5$-alkyl substituted by C$_3$-C$_{10}$-cycloalkyl which is unsubstituted or substituted by one or more substituents selected from the group consisting of C$_1$-C$_5$-alkyl, hydroxy, C$_1$-C$_5$-alkoxy and halogen, or by aryl which is unsubstituted or substituted by one or more substituents selected from the group consisting of C$_1$-C$_5$-alkyl, hydroxy, C$_1$-C$_5$-alkoxy and halogen; or represents aryl which is unsubstituted or substituted by one or more substituents selected from the group consisting of C$_1$-C$_5$-alkyl, hydroxy, C$_1$-C$_5$-alkoxy and halogen, VI) R$^6$ and R$^7$ represent H, VII) X represents —CH$_2$OR$^9$ (R$^9$ is C$_1$-C$_5$-alkyl, C$_3$-C$_{10}$-cycloalkyl, or aryl), —CH$_2$OC(=O)R$^{10}$ (R$^{10}$ is C$_1$-C$_5$-alkyl, C$_3$-C$_{10}$-cycloalkyl, or aryl), or —CH$_2$—W (W is halogen), or pharmaceutically acceptable salt thereof.

4. The compound of claim 1 wherein

I) R$^1$ represents —CH$_2$COOH,

II) R$^2$ represents C$_1$-C$_5$-alkyl,

III) R$^3$ represents H, C$_1$-C$_5$-alkyl, C$_1$-C$_5$-alkoxy, or halogen,

IV) R$^4$ represents H,

V) R$^5$ represents C$_1$-C$_5$-alkyl substituted by C$_3$-C$_{10}$-cycloalkyl which is unsubstituted or substituted by one or more substituents selected from the group consisting of C$_1$-C$_5$-alkyl, hydroxy, C$_1$-C$_5$-alkoxy and halogen, or by aryl which is unsubstituted or substituted by one or more substituents selected from the group consisting of C$_1$-C$_5$-alkyl, hydroxy, C$_1$-C$_5$-alkoxy and halogen; or represents aryl which is unsubstituted or substituted by one or more substituents selected from the group consisting of C$_1$-C$_5$-alkyl, hydroxy, C$_1$-C$_5$-alkoxy and halogen, VI) R$^6$ and R$^7$ represent H, VII) X represents —CH$_2$O-(2,3,5,6-tetrafluorophenyl), —CH$_2$O-(2,3,6-trifluorophenyl), —CH$_2$O-(2,6-difluorophenyl), —CH$_2$O-(2,6-dichlorobenzoyl) or —CH$_2$—F, or pharmaceutically acceptable salt thereof.

5. 3-2-[2-(2-Tert-butyl-benzyl)-3-oxo-2,3-dihydro-pyridazin-4-yl]-butyrylamino-5-fluoro-4-oxo-pentanoic acid.

6. 3-2-[2-(3-Tert-butyl-benzyl)-3-oxo-2,3-dihydro-pyridazin-4-yl]-butyrylamino-5-fluoro-4-oxo-pentanoic acid.

7. A pharmaceutical composition, comprising the compound as defined in claim 1 or pharmaceutically acceptable salt thereof as an active ingredient together with a pharmaceutically acceptable carrier.

8. A pharmaceutical composition, comprising the compound as defined in claim 5 or pharmaceutically acceptable salt thereof as an active ingredient together with a pharmaceutically acceptable carrier.

9. A pharmaceutical composition, comprising the compound as defined in claim 6 or pharmaceutically acceptable salt thereof as an active ingredient together with a pharmaceutically acceptable carrier.

* * * * *